US011278592B2

(12) United States Patent
Roth et al.

(10) Patent No.: US 11,278,592 B2
(45) Date of Patent: Mar. 22, 2022

(54) METHODS AND COMPOSITIONS FOR TUSC2 IMMUNOTHERAPY

(71) Applicant: BOARD OF REGENTS, THE UNIVERSITY OF TEXAS SYSTEM, Austin, TX (US)

(72) Inventors: Jack A. Roth, Houston, TX (US); Lin Ji, Sugar Land, TX (US)

(73) Assignee: Board of Regents, The University of Texas System, Austin, TX (US)

(*) Notice: Subject to any disclaimer, the term of this patent is extended or adjusted under 35 U.S.C. 154(b) by 156 days.

(21) Appl. No.: 16/341,134

(22) PCT Filed: Oct. 12, 2017

(86) PCT No.: PCT/US2017/056338
§ 371 (c)(1),
(2) Date: Apr. 11, 2019

(87) PCT Pub. No.: WO2018/071668
PCT Pub. Date: Apr. 19, 2018

(65) Prior Publication Data
US 2020/0038480 A1 Feb. 6, 2020

Related U.S. Application Data

(60) Provisional application No. 62/407,329, filed on Oct. 12, 2016.

(51) Int. Cl.
*A61P 35/00* (2006.01)
*A61K 38/17* (2006.01)
*C07K 16/28* (2006.01)

(52) U.S. Cl.
CPC ...... *A61K 38/1709* (2013.01); *C07K 16/2818* (2013.01); *C07K 2317/76* (2013.01)

(58) Field of Classification Search
CPC ............ A61K 38/1709; C07K 16/2818; C07K 2317/76; A61P 35/00
USPC ...................................................... 424/133.1
See application file for complete search history.

(56) References Cited

U.S. PATENT DOCUMENTS

| 5,844,905 | A | 12/1998 | McKay et al. |
| 5,885,796 | A | 3/1999 | Linsley et al. |
| 6,207,156 | B1 | 3/2001 | Kuchroo et al. |
| 8,008,449 | B2 | 8/2011 | Korman et al. |
| 8,017,114 | B2 | 9/2011 | Korman et al. |
| 8,119,129 | B2 | 2/2012 | Jure-Kunkel et al. |
| 8,329,867 | B2 | 12/2012 | Lazar et al. |
| 8,354,509 | B2 | 1/2013 | Carven et al. |
| 8,735,553 | B1 | 5/2014 | Li et al. |
| 9,675,663 | B2* | 6/2017 | Roth ............... A61K 48/005 |
| 2006/0251726 | A1 | 11/2006 | Lin et al. |
| 2009/0023207 | A1 | 1/2009 | Ji et al. |
| 2011/0008369 | A1 | 1/2011 | Finnefrock et al. |
| 2014/0022021 | A1 | 1/2014 | Kusachi |
| 2014/0294898 | A1 | 10/2014 | Miller et al. |
| 2014/0377339 | A1* | 12/2014 | Roth ............... A61K 38/17 424/450 |
| 2015/0065685 | A1 | 3/2015 | Arany et al. |
| 2015/0086541 | A1 | 3/2015 | Aguilar-Cordova |
| 2015/0297631 | A1 | 10/2015 | Roth et al. |

FOREIGN PATENT DOCUMENTS

| JP | 2016-528195 | 9/2016 |
| WO | WO 1995/001994 | 1/1995 |
| WO | WO 1998/042752 | 10/1998 |
| WO | WO 2000/037504 | 6/2000 |
| WO | WO 2001/014424 | 3/2001 |
| WO | WO 2005/003168 | 1/2005 |
| WO | WO 2005/009465 | 2/2005 |
| WO | WO 2006/003179 | 1/2006 |
| WO | WO 2006/072625 | 7/2006 |
| WO | WO 2006/072626 | 7/2006 |
| WO | WO 2007/042573 | 4/2007 |
| WO | WO 2008/084106 | 7/2008 |
| WO | WO 2009/101611 | 8/2009 |
| WO | WO 2010/027827 | 3/2010 |
| WO | WO 2010/065939 | 6/2010 |
| WO | WO 2011/066342 | 6/2011 |
| WO | WO 2012/071411 | 5/2012 |
| WO | WO 2012/119095 | 9/2012 |
| WO | WO 2012/160448 | 11/2012 |
| WO | WO 2014/209802 | 12/2014 |
| WO | WO 2015/016718 | 2/2015 |
| WO | WO 2015/112900 | 7/2015 |
| WO | WO 2016/049385 | 3/2016 |

OTHER PUBLICATIONS

Clinical Trial Record for NCT01455389, retrieved from the Internet: URL: <https://clinicaltrials.gov/ct2/history/NCT01455389?V_11=View#StudyPageTop>, 2016.
Deng et al., "Lactotransferrin acts as a tumor suppressor in nasopharyngeal carcinoma by repressing AKT through multiple mechanisms", *Oncogene*, 32:4273-4283, 2013.
Deng et al., "Synergistic Tumor Suppression by Coexpression of FUS1 and p53 Is Associated with Down-regulation of Murine Double Minute-2 and Activation of the Apoptotic Protease-Activating Factor 1-Dependent Apoptotic Pathway in Human Non-Small Cell Lung Cancer Cells", *Cancer Res.*, 67(2):709-717, 2007.
Extended European Search Report issued in corresponding European Application No. 17861125, dated May 4, 2020.
Gray et al., "Phosphatidylserine-targeting antibodies augment the anti-tumorigenic activity of anti-PD-1 therapy by enhancing immune activation and downregulating pro-oncogenic factors induced by T-cell checkpoint inhibition in murine triple-negative breast cancers", *Breast Cancer Res.*, 18(50):2016.

(Continued)

*Primary Examiner* — Yan Xiao
(74) *Attorney, Agent, or Firm* — Parker Highlander PLLC

(57) ABSTRACT

A method of treating a subject having a cancer comprising administering a tumor suppressor therapy, such as a TUSC2 therapy, in conjunction with an immune checkpoint inhibitor. Kits and reagents for use in cancer therapy are also provided.

13 Claims, 19 Drawing Sheets

(56) References Cited

OTHER PUBLICATIONS

Hurwitz et al., "CTLA-4 blockade synergizes with tumor-derived granulocyte-macrophage colony-stimulating factor for treatment of an experimental mammary carcinoma", *Proc. Natl. Acad. Sci. U.S.A.*, 95(17):10067-10071, 1998.
International Search Report and Written Opinion issued in corresponding PCT Application No. PCT/US2017/056338, dated Dec. 26, 2017.
Ito et al., "Liposomal vector mediated delivery of the 3p FUS1 gene demonstrates potent antitumor activity against human lung cancer in vivo", *Cancer Gene Ther.*, 11:733-739, 2004.
Ivanova et al., "Autoimmunity, spontaneous tumourigenesis, and IL-15 insufficiency in mice with a targeted disruption of the tumour suppressor gene Fus1", *J. Pathol.*, 211:591-601, 2007.
Kawashima et al., "Synergistic inhibition of EFGR tyrosine kinase activity and NSCLC cell growth by combination treatment with FUS1-nanoparticle and gefitinib", *Proc. Amer. Assoc. Cancer Res.*, 46:637, abstract #2707, 2005.
Larkin et al., "Combined Nivolumab and Ipilimumab or Monotherapy in Untreated Melanoma", *N. Engl. J. Med.*, 373:23-24, 2015.
Lerman et al., "The 630-kb Lung Cancer Homozygous Deletion Region on Human Chromosome 3p21.3: Identification and Evaluation of the Resident Candidate Tumor Suppressor Genes", *Cancer Res.*, 60:6116-6133, 2000.
Lowe et al., "Intrinsic tumour suppression", *Nature*, 432:307-315, 2004.
Lu et al., "Phase I clinical trial of systemically administered TUSC2 (FUS1)-nanoparticles mediating functional gene transfer in humans", *PLoS One*, 7(4):e34833, 2012.
Mellman et al., "Cancer inununotherapy comes of age", *Nature*, 480:480-489, 2011.
Okazaki and Honjo, "PD-1 and PD-1 ligands: from discovery to clinical application", *Intern. Immun.*, 19(7):813, 2007.
Orr et al., "Ly49H signaling through DAP10 is essential for optimal natural killer cell responses to mouse cytomegalovirus infection", *J. Exper. Med.*, 206:807-817, 2009.
Pardoll, "The blockade of immune checkpoints in cancer inununotherapy", *Nat. Rev. Cancer*, 12:252-264, 2012.
Roth, "Adenovirus p53 gene therapy", *Exp. Opin. Biol. Ther.*, 6:55-61, 2006.
Shevach and Stephens, "The GITR-GITRL interaction: co-stimulation or contrasuppression of regulatory activity?", *Nat. Rev. Immunol.*, 6:613-618, 2006.
Uzhachenko et al., "Fus1/Tusc2 Is a Novel Regulator of Mitochondrial Calcium Handling, $Ca^{2+}$-Coupled Mitochondrial Processes, and $Ca^{2+}$-Dependent NFAT and NF-jB Pathways in $CD4^+$ T Cells", *Antiox. Redox Signal.*, 20(10):1533-1547, 2014.
Uzhachenko et al., "Mitochondria, calcium, and tumor suppressor Fus1: At the crossroad of cancer, inflammation, and autoimmunity", *Oncotarget*, 6(25):20754-20772, 2015.
Meraz et al., "Abstract 621: Tumor suppressor TUSC2 immunogene therapy is synergistic with anti-PD1 in lung cancer syngeneic mouse models," *Cancer Res*, 77(13Suppl):Abstract 621, 2017.
Meraz et al., "TUSC2 Immunogene Therapy Synergizes with Anti-PD-1 through Enhanced Proliferation and Infiltration of Natural Killer Cells in Syngeneic Kras-Mutant Mouse Lung Cancer Models," *Cancer Immunology Research*, 6(2):163-177, 2018.
Office Action issued in Japanese Application No. 2019-519701, dated Sep. 1, 2021, and English language translation thereof.

\* cited by examiner

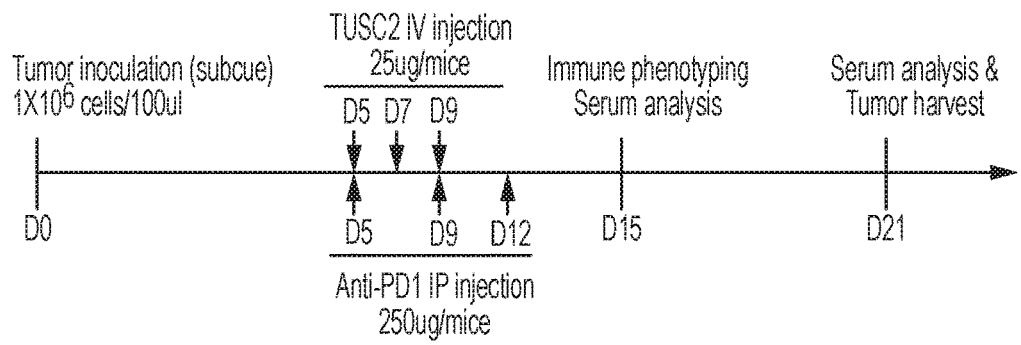
FIG. 1A
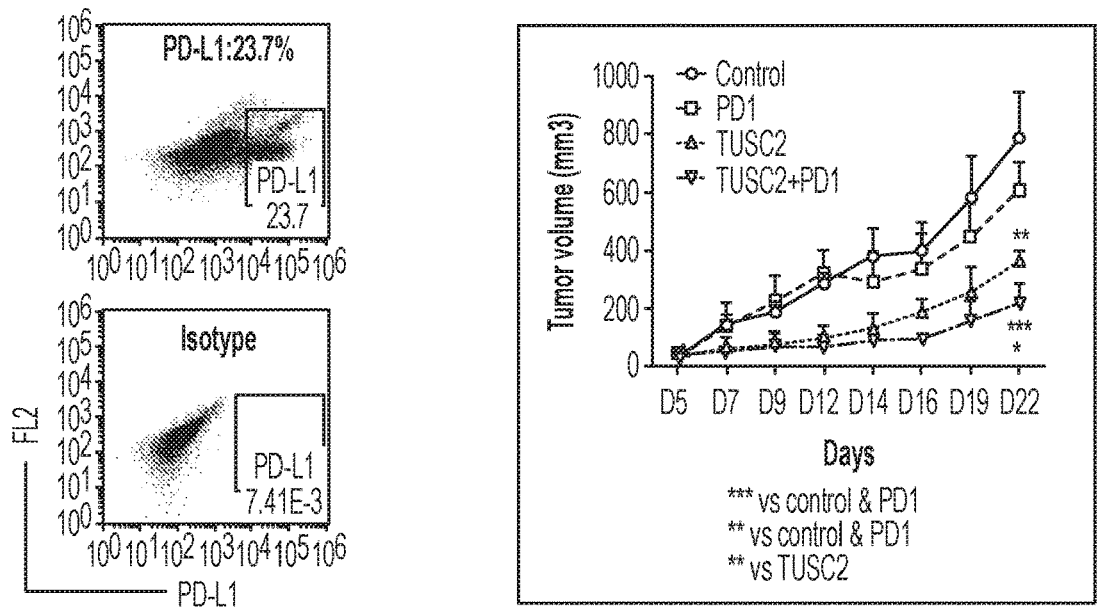
FIG. 1B
FIG. 1C
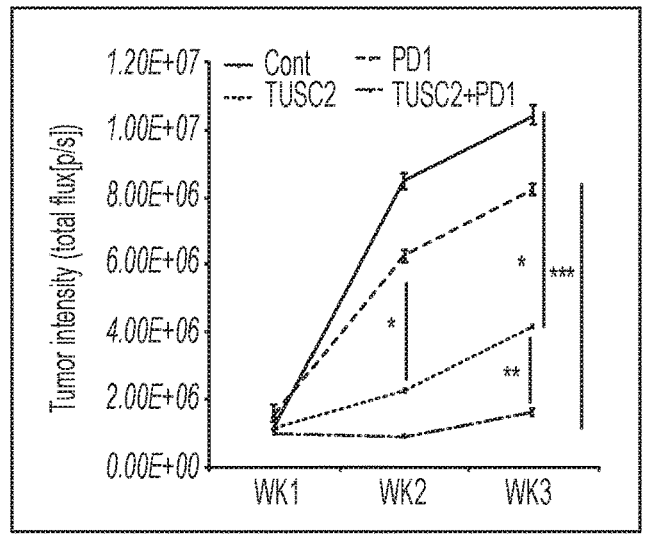
FIG. 1D

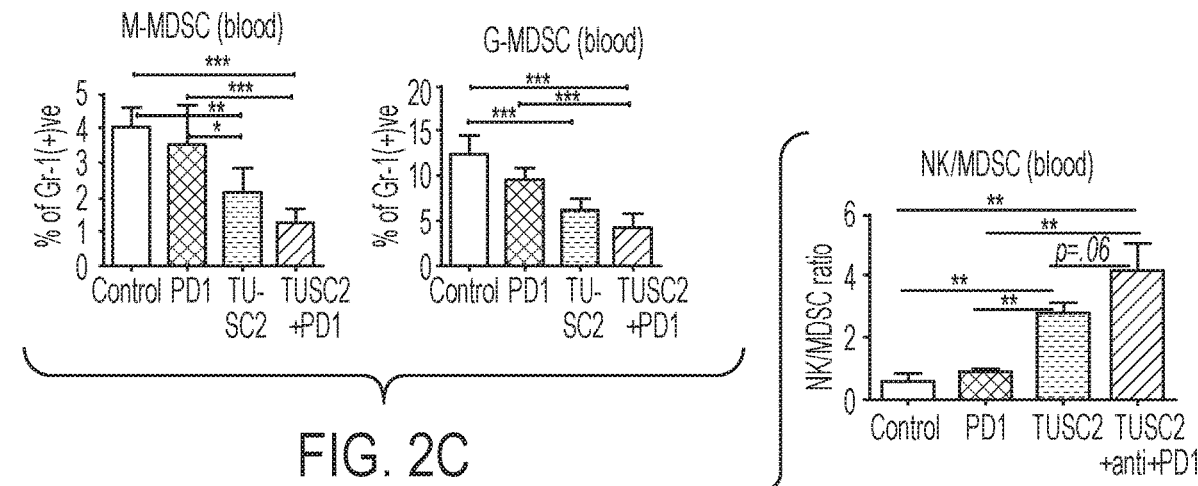
FIG. 2C
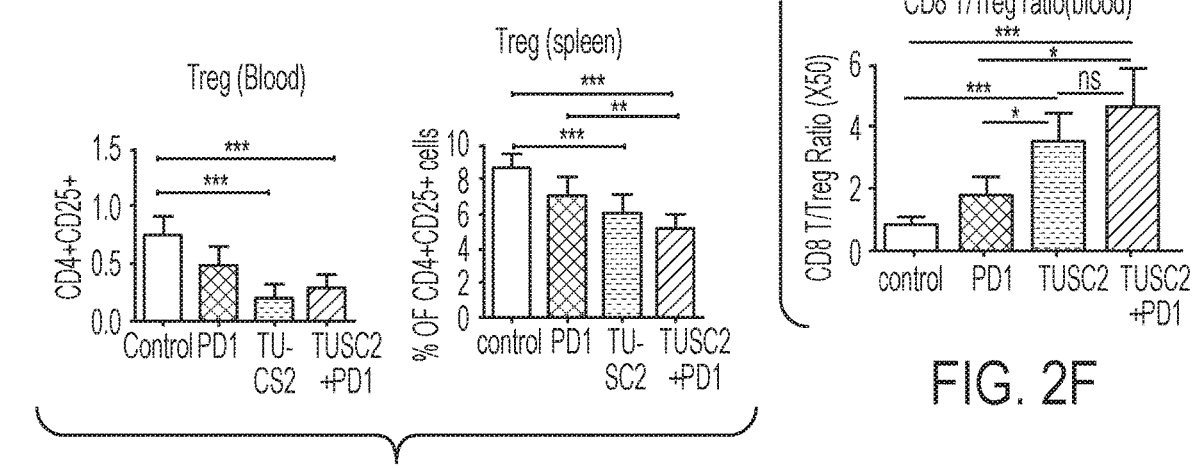
FIG. 2D
FIG. 2F
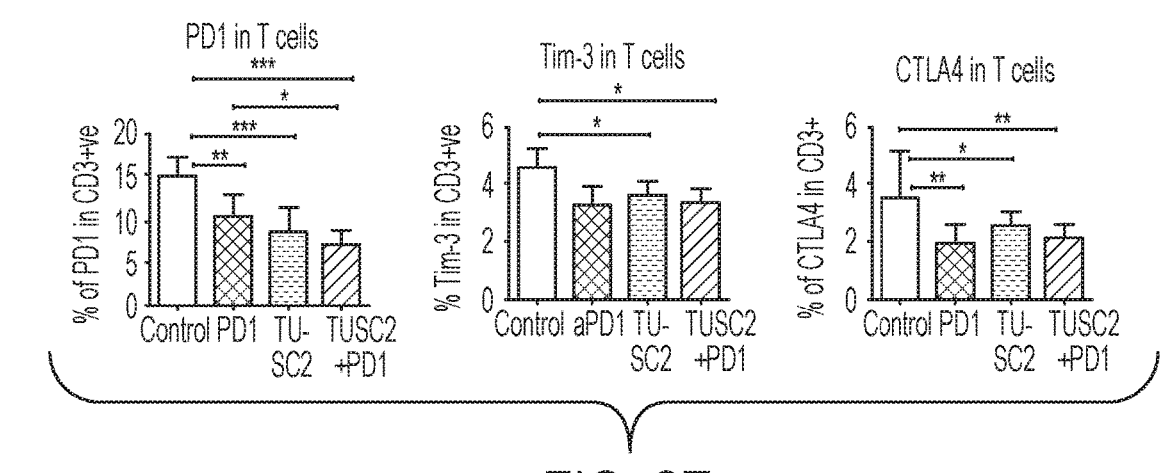
FIG. 2E

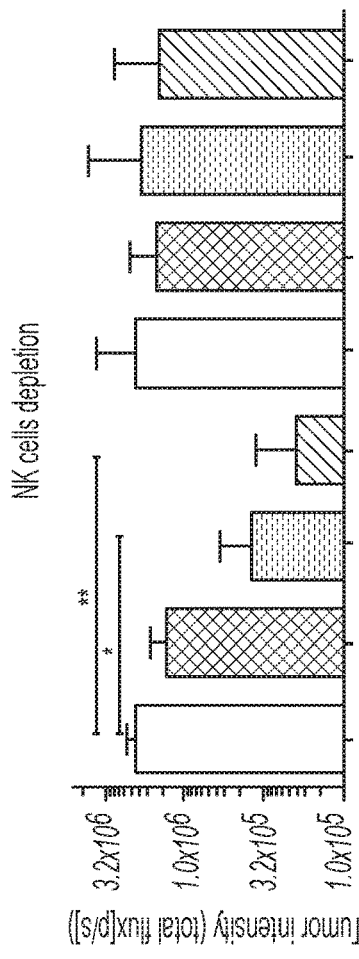
FIG. 4A
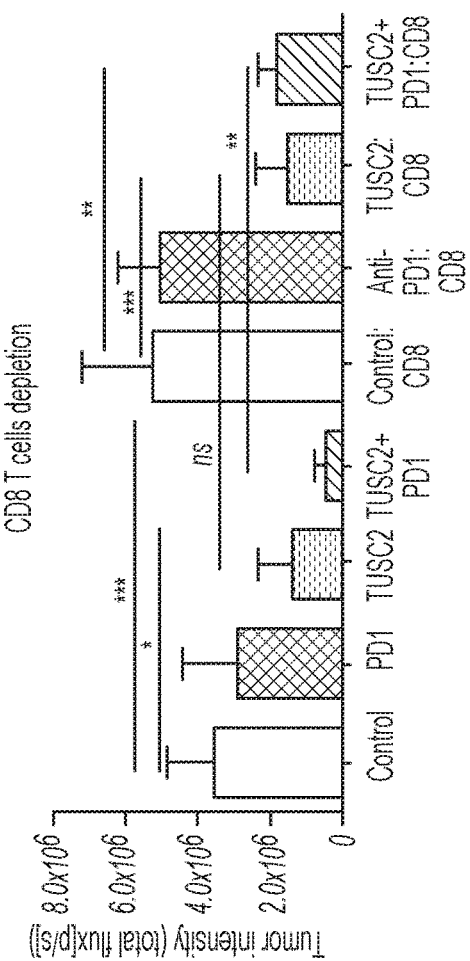
FIG. 4B
FIG. 4C
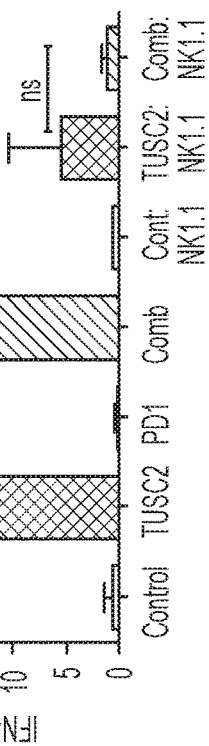

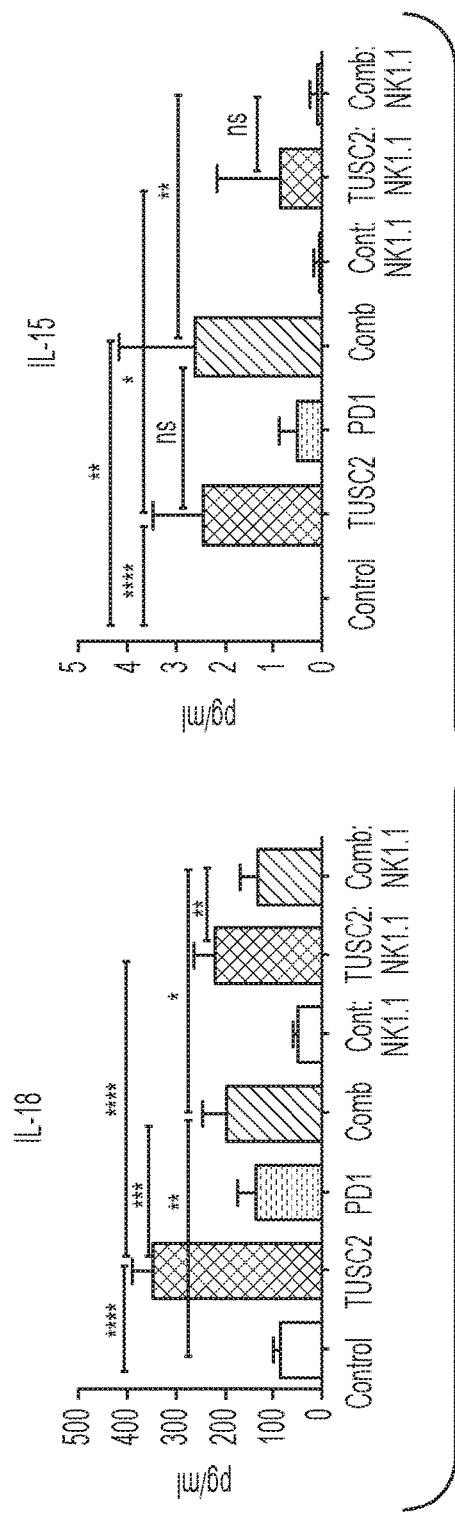
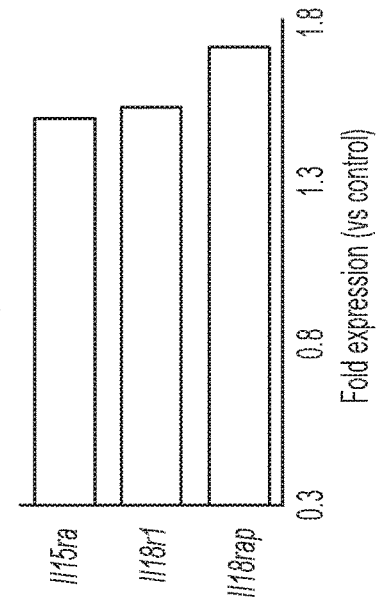
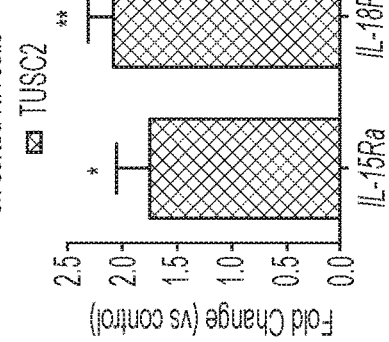
FIG. 4D
FIG. 4E
FIG. 4F

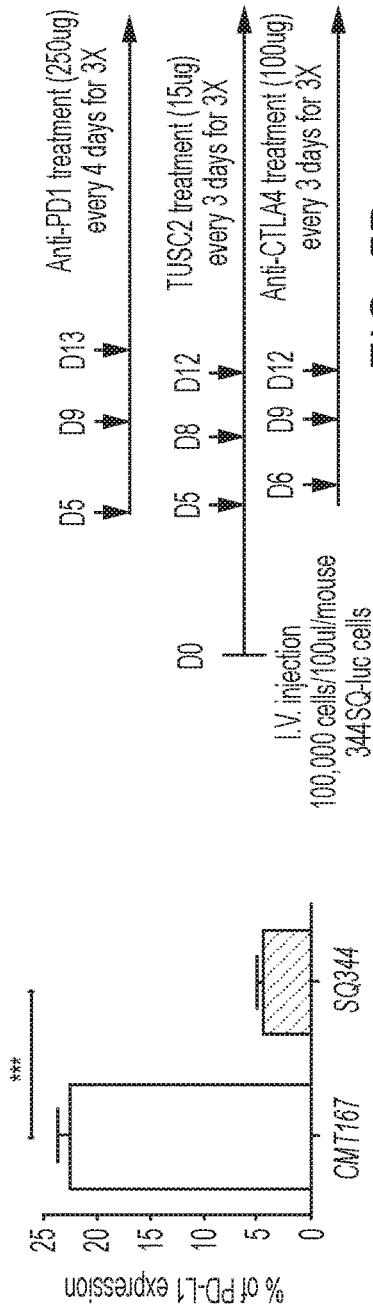
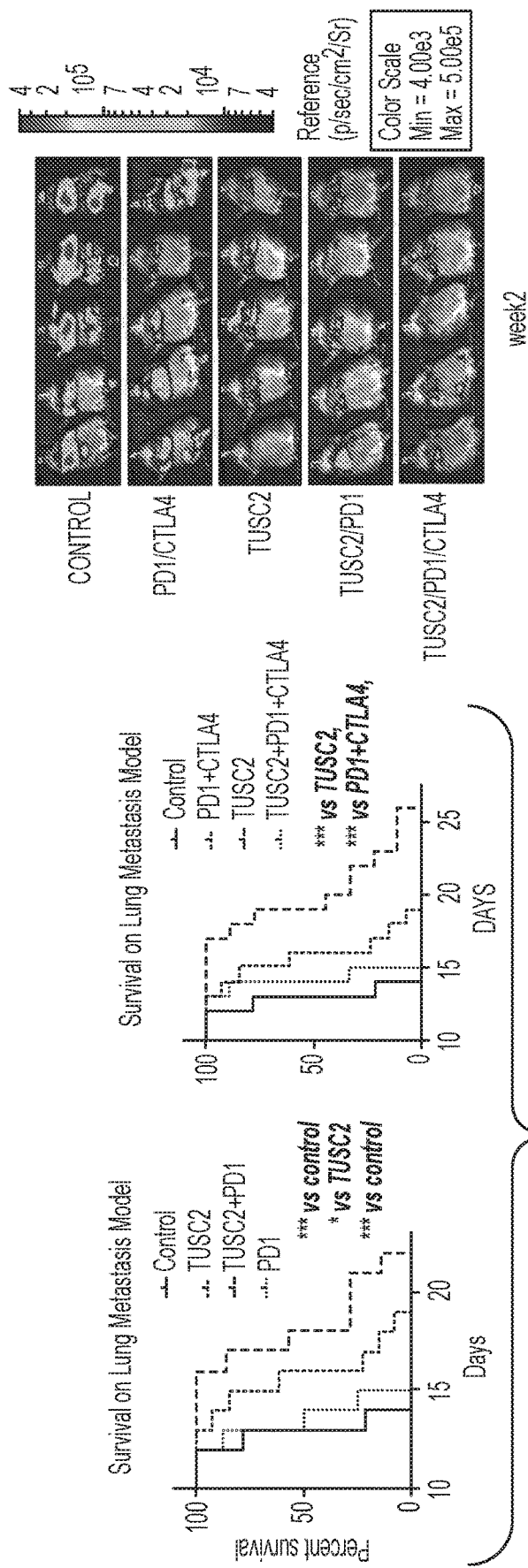
FIG. 5A
FIG. 5B
FIG. 5C
FIG. 5D

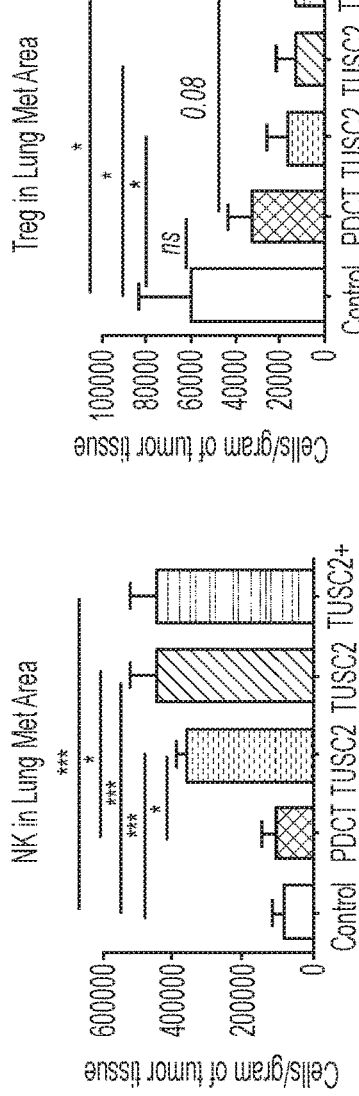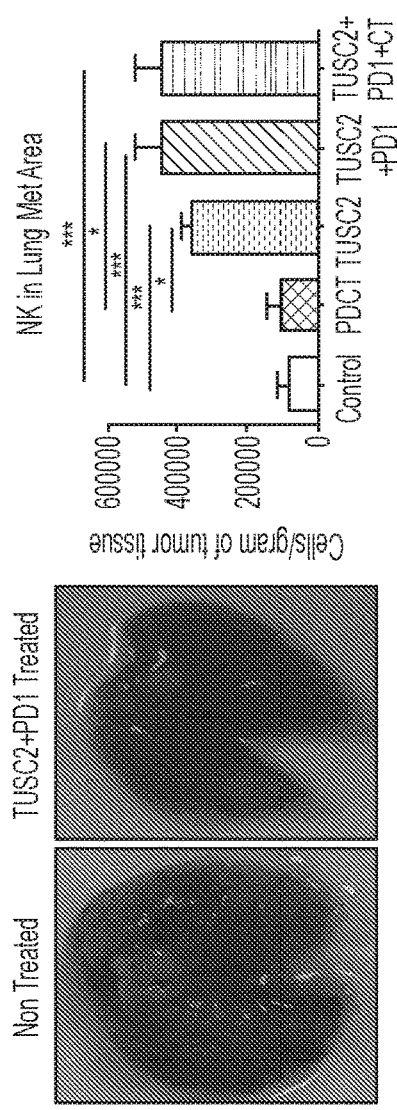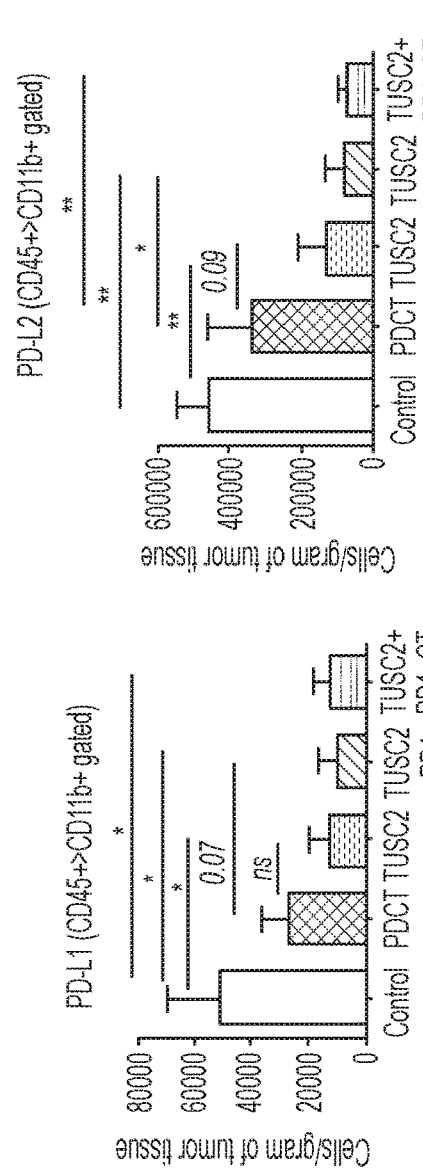
FIG. 5E  FIG. 5F  FIG. 5G  FIG. 5H  FIG. 5I

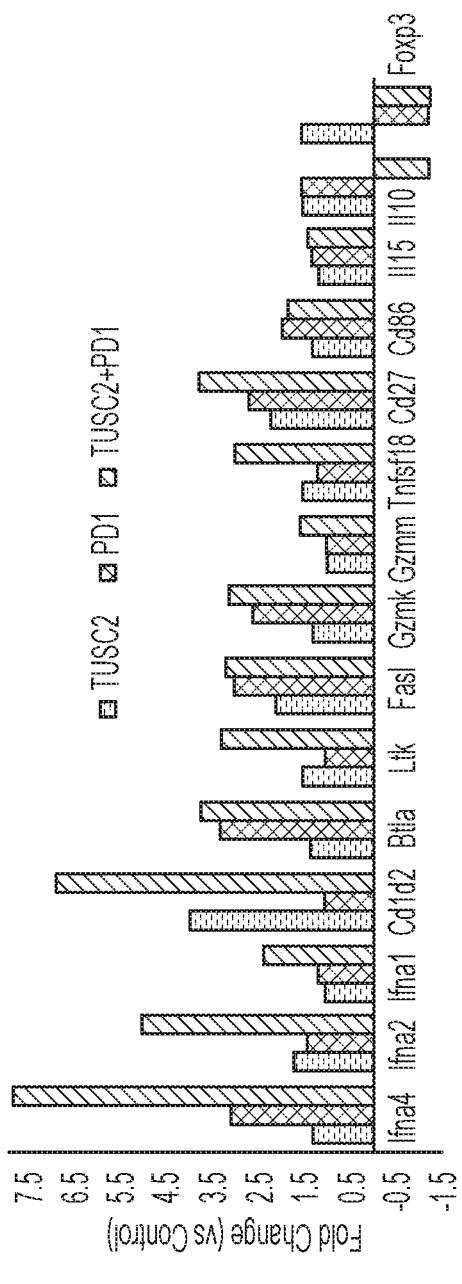
FIG. 6C
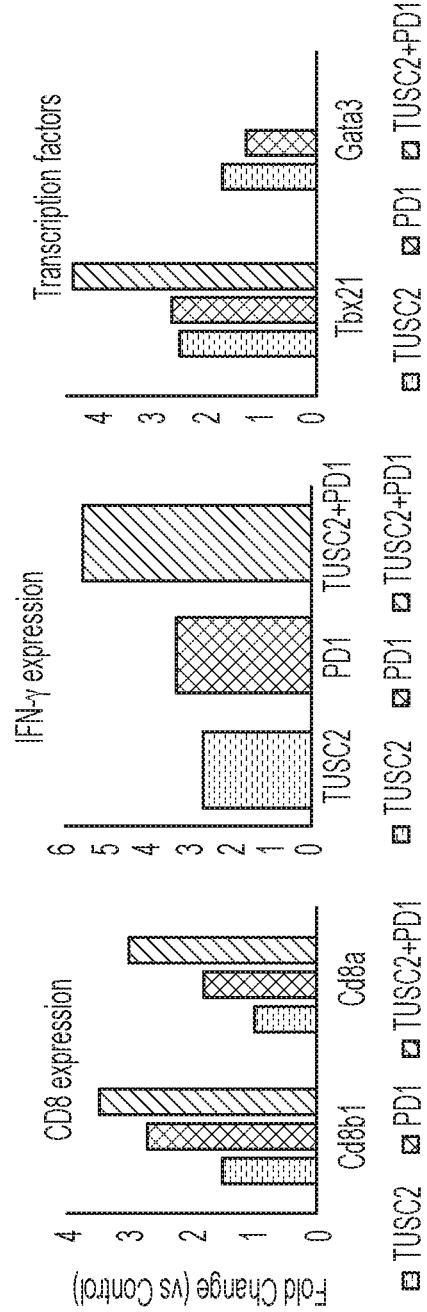
FIG. 6D
FIG. 6E
FIG. 6F

Supplement 4

| | | PD1 vs Combination | |
| --- | --- | --- | --- |
| | | p-value | Fold change |
| ↑ | Cd1d2 | 0.006 | 7.21 |
| ↑ | Ltf | 0.017 | 3.01 |
| ↑ | H60a | 0.046 | 2.54 |
| ↑ | Klra21 | 0.018 | 2.53 |
| ↑ | Tnfsf18 | 0.049 | 2.5 |
| ↑ | Bcl6 | 0.044 | 1.5 |
| ↓ | Il12rb2 | 0.026 | -6.18 |
| ↓ | Cd59b | 0.05 | -3.94 |
| ↓ | Ccl1 | 0.025 | -3.5 |
| ↓ | Ncr1 | 0.024 | -2.5 |
| ↓ | Klra5 | 0.031 | -2.2 |
| ↓ | Egr3 | 0.016 | -2.18 |
| ↓ | Cd46 | 0.027 | -1.6 |

FIG. 10

METHODS AND COMPOSITIONS FOR TUSC2 IMMUNOTHERAPY

This application is a national phase application under 35 U.S.C. § 371 of International Application No. PCT/US2017/056338, filed Oct. 12, 2017, which claims the benefit of United States Provisional Patent Application No. 62/407,329, filed Oct. 12, 2016, the entirety of each of which is incorporated herein by reference.

BACKGROUND OF THE INVENTION

1. Field of the Invention

The present embodiments provided herein relate generally to the fields of molecular biology, immunology and cancer therapy.

2. Description of Related Art

As the molecular and genetic mechanisms of oncogenesis become better elucidated, the focus of cancer therapy has shifted from the tissue to the genetic level (Bishop, 1991). Mutations in two major classes of genes, oncogenes and tumor suppressor genes (TSGs), play central roles in the oncogenic process. TSGs appear to require homozygous deletion or mutation for inactivation, and restoration of TSG expression is feasible in human tumors (Lowe et al., 2004; Roth, 2006). Homozygous deletions in the 3p21.3 region in lung cancer cell lines and primary lung tumors have led to the identification of multiple genes with tumor suppressor activity from this region (Lerman et al., 2000). These deletions have led to the development of targeted anti-cancer therapies. However, it remains unclear how the efficacy of such therapies could be enhanced.

SUMMARY OF THE INVENTION

In a first embodiment, there is provided a method of treating a subject having a cancer comprising administering a tumor suppressor therapy (e.g., a TUSC2 therapy) in conjunction with an immune checkpoint inhibitor. Thus, a method is provided for treating a subject having a cancer, wherein the subject is being treated with (or was previously administered) at least one immune checkpoint inhibitor, the method comprising administering a tumor suppressor therapy, such as a TUSC2 therapy, to the subject. For example, a subject to be treated with a TUSC2 therapy can be a subject who was administered an immune checkpoint inhibitor less that one hour, 6 hours, 12 hours, 1 day, 3 days, one week or two weeks before administration of the TUSC2 therapy. As used herein, a TUSC2 therapy can be any type of therapy that provides or causes expression of a TUSC2 polypeptide in a cancer cell (see, e.g., U.S. Pat. No. 7,902,441, incorporated herein by reference). For example, a TUSC2 therapy may comprise delivery of a TUSC2 polypeptide or TUSC2 expression vector to cancer cell. A therapy may, for instance, be delivered via nanoparticles, or in the case of nucleic acid expression vectors, through the use of a viral vector.

In certain embodiments, a method is provided for treating a subject having a cancer, comprising administering to the subject a TUSC2 therapy in conjunction with at least one immune checkpoint inhibitor. For instance, the TUSC2 therapy can be administered, before, after or essentially concomitantly with the at least one immune checkpoint inhibitor. Thus, in some embodiments, a composition is provided comprising a TUSC2 therapeutic and an immune checkpoint inhibitor in a therapeutically effective amount to treat a cancer.

In some aspects, the at least one checkpoint inhibitor is selected from an inhibitor of CTLA-4, PD-1, PD-L1, PD-L2, LAG-3, BTLA, B7H3, B7H4, TIM3, KIR, or A2aR. In certain aspects, the at least one immune checkpoint inhibitor is a human programmed cell death 1 (PD-1) axis-binding antagonist. In some aspects, the PD-1 axis-binding antagonist is selected from the group consisting of a PD-1 binding antagonist, a PDL-binding antagonist and a PDL2-binding antagonist. In certain aspects, the PD-1 axis-binding antagonist is a PD-1-binding antagonist. In some aspects, the PD-1-binding antagonist inhibits the binding of PD-1 to PDL1 and/or PDL2. In particular aspects, the PD-1-binding antagonist is a monoclonal antibody or antigen binding fragment thereof. In specific aspects, the PD-1-binding antagonist is nivolumab, pembrolizumab, pidillizumab, KEYTRUDA®, AMP-514, REGN2810, CT-011, BMS 936559, MPDL3280A or AMP-224. In some aspects, the at least one immune checkpoint inhibitor is an anti-CTLA-4 antibody. In particular aspects, the anti-CTLA-4 antibody is tremelimumab, YERVOY®, or ipilimumab. In certain aspects, the at least one immune checkpoint inhibitor is an anti-killer-cell immunoglobulin-like receptor (KIR) antibody. In some aspects, the anti-KIR antibody is lirilumab. In certain aspects, the subject has been or is being administered more than one immune checkpoint inhibitors, such as an anti-PD1 antibody and an anti-CTLA4 antibody.

In certain embodiments, administration of a TUSC2 therapy comprises administration of a TUSC2 expression vector, such a DNA plasmid encoding TUSC2. An expression vector for use according to the embodiments provided herein will generally comprise control elements for the expression of the TUSC2 coding sequence. For example, a vector can comprise a promoter and enhancer element that are effective for expression in cancer cell of interest. In certain aspects, for instance, TUSC2 expression is provided by a CMV promoter or recombinant version thereof, such as the CMV promoter construct described in U.S. Patent Publication No. 20070092968, incorporated herein by reference. In certain embodiments, a vector provided herein comprises a modified CMV promoter. In certain embodiments, a vector provided herein comprises a mini-CMV promoter. Additional expression control elements can be included such as, for example, an intron, a drug response element, a RNA stabilizing or destabilizing sequence, a cellular localization signal, a polyadenylation signal sequence and/or an optimized translation start codon. Plasmid DNA vectors may also comprise sequences that help facilitate DNA production, such as, a bacterial origin of replication and/or a drug resistance marker. In certain specific aspects, the TUSC2 expression vector is the pLJ143/KGB2/FUS1 plasmid.

Methods for delivery of an expression vector to cells (e.g., in vivo delivery) are well known in the art and include, without limitation, nanoparticles (e.g., liposome nanoparticles), lipid conjugates and viral vectors. In certain aspects, a TUSC2 expression vector is administered in a nanoparticle, such as N-[1-(2,3-dioleoyloxy)propyl]-N,N,N-trimethylammonium chloride (DOTAP):cholesterol liposome nanoparticle. A skilled artisan will recognize that various properties of liposomes can be adjusted to optimize vector delivery. For example, the liposomes may be adjusted to have a certain size range and/or a particular ratio of DNA to lipid; DNA to cholesterol; or lipid to cholesterol. For instance, in the case of a DOTAP:cholesterol liposome, the DOTAP:cholesterol ratio can be defined as between about 1.5:1 and 1:1.5, such as about 10:9. In further aspects, a TUSC2 expression vector is provided in a liposome nanoparticle, wherein the nanoparticles comprise an average particle size of between about 50 and about 500 nm (e.g., 200-500 nm). In still further aspects, a TUSC2-nanoparticle formulation can be defined by their optical density (OD), such as having $OD_{400}$ of between about 0.65 and 0.95.

In still further embodiments, a TUSC2 therapy can comprise administration of a TUSC2 polypeptide. Methods for administration of TUSC2 polypeptide are described for example in U.S. Publication Nos. 20060251726 and 20090023207, incorporated herein by reference. A TUSC2 polypeptide may be modified to enhance its activity and/or ability to enter cancer cells. For instance, the polypeptide can be modified with a lipid moiety (e.g., myristoylated). In certain aspects a TUSC2 in provided as a nanoparticle (e.g., a lipid-based nanoparticle) such as, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube.

A TUSC2 therapy and/or an immune checkpoint inhibitor according to the embodiments provided herein is typically formulated in a pharmaceutically acceptable carrier. A therapy according to the embodiments may be delivered, for example, intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, via inhalation (e.g. aerosol inhalation), by injection or by infusion, and the route of delivery can depend upon the type of cancer to be treated. For example, a TUSC2 expression vector complexed with DOTAP:cholesterol liposome can be administer via intravenous infusion. In certain specific aspects, a TUSC2 therapy is administered intravenously in a dose of from about 0.01 mg/kg to about 0.10 mg/kg, such as a dose of about 0.02, 0.03, 0.04, 0.05, 0.06, 0.07, 0.08 0.09 or 0.10 mg/kg. In further aspects, a TUSC2 therapy, can be administer two or more times (e.g., 3, 4, 5, 6, 7, 8, 9 or 10 times). The timing between doses of such a therapy can be varied and can include, without limitation, about 1, 2 or 3 days, about 1, 2, or 3 weeks or 1 month or more between doses.

In yet a further embodiment, there is provided a method for treating a subject having a cancer, comprising administering a TUSC2 therapy to the subject in conjunction at least one immune checkpoint inhibitor and/or in conjunction with one or more anti-inflammatory agent. For example, the anti-inflammatory agent may be administered before, after or during a TUSC2 therapy. In a further aspect, more than one anti-inflammatory agent is administered, such as administration of an antihistamine and a corticosteroid. Thus, in certain specific aspects the anti-inflammatory for use in conjunction with a TUSC2 therapy is diphenhydramine and/or dexamethasone.

In further embodiments, a method provided herein further comprises administering a further anticancer therapy. The further anticancer therapy may be, without limitation, a surgical therapy, chemotherapy (e.g., administration of a protein kinase inhibitor or a EGFR-targeted therapy), radiation therapy, cryotherapy, hyperthermia treatment, phototherapy, radioablation therapy, hormonal therapy, immunotherapy, small molecule therapy, receptor kinase inhibitor therapy, anti-angiogenic therapy, cytokine therapy or a biological therapies such as monoclonal antibodies, siRNA, antisense oligonucleotides, ribozymes or gene therapy. Without limitation the biological therapy may be a gene therapy, such as tumor suppressor gene therapy, a cell death protein gene therapy, a cell cycle regulator gene therapy, a cytokine gene therapy, a toxin gene therapy, an immunogene therapy, a suicide gene therapy, a prodrug gene therapy, an anti-cellular proliferation gene therapy, an enzyme gene therapy, or an anti-angiogenic factor gene therapy.

Thus, in yet a further embodiment provided herein are compositions, therapies, and methods for treating a subject having a cancer, comprising administering to the subject a TUSC2 therapy (e.g., a TUSC2 polypeptide or a TUSC2 expression vector) in conjunction with an immune checkpoint inhibitor and a further anticancer agent, such as a chemotherapeutic. For example, the chemotherapeutic can be a protein kinase inhibitor, such as a Src or Akt kinase inhibitor. In some aspects, the chemotherapeutic is an epidermal growth factor receptor (EGFR) inhibitor.

Thus, in certain embodiments, a method is provided for treating a subject having a cancer, comprising administering to the subject a TUSC2 therapy in conjunction with at least one immune checkpoint inhibitor and, optionally, a protein kinase inhibitor. For instance, the TUSC2 therapy and/or the immune checkpoint inhibitor can be administered, before, after or essentially concomitantly with the protein kinase inhibitor. Thus, in some embodiments, a composition is provided comprising a TUSC2 therapeutic, an immune checkpoint inhibitor and a protein kinase inhibitor in a therapeutically effective amount to treat a cancer. Protein kinase inhibitors for use according to the embodiments include, without limitation, EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. For example, the protein kinase inhibitor can be Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016, or a mixture thereof. In certain aspects, the protein kinase inhibitor is an AKT inhibitor (e.g., MK-2206, GSK690693, A-443654, VQD-002, Miltefosine or Perifosine).

EGFR-targeted therapies for use in accordance with the embodiments include, but are not limited to, inhibitors of EGFR/ErbB1/HER, ErbB2/Neu/HER2, ErbB3/HER3, and/or ErbB4/HER4. A wide range of such inhibitors are known and include, without limitation, tyrosine kinase inhibitors active against the receptor(s) and EGFR-binding antibodies or aptamers. For instance, the EGFR inhibitor can be gefitinib, erlotinib, cetuximab, matuzumab, panitumumab, AEE788; CI-1033, HKI-272, HKI-357 or EKB-569. In certain embodiments, the compositions and therapies provided herein are administered systemically or locally. In one embodiment, the compositions and therapies provided herein are administered systemically. In certain aspects, an EGFR inhibitor is administered to a patient before, after or essentially concomitantly with a TUSC2 therapy. For example, the therapies may be co-administered, such as by co-administration in an intravenous infusion. In certain embodiments, TUSC2 and EGFR inhibitors can be administered in any amount effective to treat cancers. In certain embodiments, the compositions, therapies, and methods provided herein comprise administering TUSC2 and EGFR inhibitors in lower doses than either composition administered alone. In certain embodiments, the compositions, therapies, and methods comprise administering TUSC2 and EGFR inhibitors in lower doses that reduce side effects. In certain embodiments, the compositions, therapies, and methods comprise administering a TUSC2 therapy, an immune checkpoint inhibitor and EGFR inhibitors in doses effective to provide additive, cooperative, or synergistic effect than that provided by either composition administered alone. In certain aspects, cancers for treatment with such therapies can be any of those described herein, such as lung cancers (e.g., non-small cell lung cancer). In certain preferred aspects, a cancer for treatment with a combination therapy is an EGFR-expressing cancer. In certain embodiments, the EGFR-expressing cancer comprises at least 1%, 5%, 10%, 15%, 20%, 25%, 30%, 35%, 40%, 45%, 50%, 55%, 65%, 70%, 75%, 80%, 85%, 90%, 95%, 96%, 97%, 98%, or 99% tumor cells expressing EGFR.

In yet still a further embodiment provided herein is a method for treating a subject having a cancer, wherein it was previously determined that the cancer expresses an EGFR, the method comprising administering to the subject a TUSC2 therapy in conjunction with an immune checkpoint inhibitor and an EGFR inhibitor. In certain embodiments, provided herein is a method for treating a subject having a cancer comprising the step of determining whether the cancer expresses an EGFR, and administering to the subject a TUSC2, an immune checkpoint inhibitor and an EGFR inhibitor. Methods for assessing the EGFR-expression status of a cancer have been described, for example in U.S. Patent Publn. No. 20110052570, incorporated herein by reference. In certain aspects, the EGFR-expressing cancer can be a cancer that expresses a mutant EGFR, such as a cancer expressing an EGFR having a L858R and/or T790M mutation. In certain embodiments, the compositions and therapies provided herein are administered to the patient that have an EGFR-expressing cancer that comprises at least 1%, 5%, 10%, 15%, 20%, 25%, 30%, 35%, 40%, 45%, 50%, 55%, 65%, 70%, 75%, 80%, 85%, 90%, 95%, 96%, 97%, 98%, or 99% tumor cells expressing EGFR. In still further aspects, the subject for treatment has a cancer that was previously determined to express an EGFR and in which at least 10% of the cells of the cancer are apoptotic. In certain embodiments, the methods provided herein further comprise determining whether at least 10%, 15%, 20%, 25%, 30%, 35%, 40%, 45%, 50%, 55%, 65%, 70%, 75%, 80%, 85%, 90%, 95%, 96%, 97%, 98%, or 99% of the cells of the EGFR-expressing cancer are apoptotic.

In certain embodiments, a cancer for treatment or assessment may present as a tumor, such as primary or metastatic tumor. A cancer may be an early stage cancer, or may be a metastatic or late stage cancer. In certain aspects, the cancer is an oral cancer, oropharyngeal cancer, nasopharyngeal cancer, respiratory cancer, a urogenital cancer, a gastrointestinal cancer, a central or peripheral nervous system tissue cancer, an endocrine or neuroendocrine cancer, a hematopoietic cancer, a glioma, a sarcoma, a carcinoma, a lymphoma, a melanoma, a fibroma, a meningioma, brain cancer, oropharyngeal cancer, nasopharyngeal cancer, renal cancer, biliary cancer, prostatic cancer, pheochromocytoma, pancreatic islet cell cancer, a Li-Fraumeni tumor, thyroid cancer, parathyroid cancer, pituitary tumors, adrenal gland tumors, osteogenic sarcoma tumors, multiple neuroendrcine type I and type II tumors, breast cancer, lung cancer (e.g., a non-small cell lung cancer (NSCLC) or small cell lung cancer (SCLC)), head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In further aspects, a cancer may be defined as a cancer that is resistant to one or more anticancer therapy, such a chemotherapy resistant cancer. For example, the cancer may be a cancer that is resistant to a platinum-based chemotherapeutic, such as cisplatin.

In some aspects of the above embodiments, administering the TUSC2 therapy and at least one immune checkpoint inhibitor results in an increase of NK and/or $CD8^+$ T cell density in the tumor. In specific aspects, the CD8+ T cell density increases by at least 3-fold, such as 4-, 5, 6, 7-, 8-, 9- or 10-fold. In some aspects, administering the TUSC2 therapy and at least one immune checkpoint inhibitor results in CcL3, CcL4, CcL21a, and/or CcL19 serum levels.

In still further embodiments provided herein is a kit comprising a TUSC2 therapeutic and at least one immune checkpoint inhibitor. For example, in some aspects, a kit provided herein comprises a TUSC2 therapeutic, at least one immune checkpoint inhibitor and a reagent for testing a subject to determine their response for the TUSC2 therapeutic and/or the immune checkpoint inhibitor. For example, the reagent for testing a subject to determine their response for the TUSC2 therapeutic can be a reagent for determining the level of apoptosis in cancer cells of the subject. In further aspects, a kit further comprises one or more anti-inflammatory agents or a kinase inhibitor. In still further aspects the kit may comprise one more additional components including, but not limited to, a pharmaceutically acceptable dilution agent, a syringe, an infusion bag, an infusion line, and/or a set of instruction for use of the kit.

It is contemplated that any method or composition described herein can be implemented with respect to any other method or composition described herein. Likewise, aspects of the present embodiments discussed in the context of a method for treating a subject are equally applicable to a method of predicting response in a subject and vice versa.

The use of the word "a" or "an" when used in conjunction with the term "comprising" in the claims and/or the specification may mean "one," but it is also consistent with the meaning of "one or more," "at least one," and "one or more than one."

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1E: Enhanced anti-tumor activity was found by TUSC2 and anti-PD1 combination treatment on CMT167 subcutaneous model. (A) Sequential treatment strategy showing the tumor inoculation, treatment schedules and doses, blood and spleen collection for immune cell analysis and tumor harvest for immunohistochemistry as well as RNA isolation. (B) Surface expression level of PD-L1 on CMT167-luc cells was determined by flow cytometry. (C), (D) Tumor growth curves for four different treatment groups (N=10 mice/group) were determined based on tumor volume & bioluminescence intensity generated from small animal imaging by IVIS 200. The control group was treated with nanovesicles loaded with empty (no TUSC2 gene) vector. The TUSC2+PD1 therapy resulted in the highest inhibition of tumor growth, followed by TUSC2, PD1, and control. (E) Representative images of tumor bearing mice from each treatment group with bioluminescence signals taken by IVIS 200 imaging. The data is representative of four independent experiments. CONTRAST statement in PROC MIXED procedure in SAS was used to compare the imaging intensity among treatment groups. SAS version 9.4 and S-Plus version 8.04 were used to carry out the computations for all analyses. Statistics were shown at a significance level of $p<0.05$ unless otherwise noted. *, $P<0.05$, , $P<0.01$, *, $P<0.001$ FIGS. 2A-2F: Combined TUSC2 and anti-PD1 upregulates natural killer and cytotoxic T cells and downregulates regulatory cells. TUSC2+anti-PD1 treatment altered immune cell populations in peripheral blood and spleen. The control group was treated with nanovesicles loaded with empty (no TUSC2 gene) vector. (A) Effect of TUSC2 on NK, T cells and B cells on tumor free mice. Pooled samples of n=3 mice/group were used for flow cytometry analysis. In vivo uptake of TUSC2 nanovesicles were determined based on exogenous TUSC2 expression. 24 h after intravenous injection of TUSC2 nanovesicles, four different immune populations (T cells, B cells, NK cells & Lin negative cells) were sorted from spleen and RT-PCR were performed to determine the expression of TUSC2. (B) Effect of TUSC2 and TUSC2+anti-PD1 treatments on Natural Killer (NK), T cell and B cells at week 2 of tumor implantation. (C) TUSC2 treatment altered MDSC status. Monocytic and granulocytic MDSC were determined using the following gating strategy; CD45+>CD3->MHCII low>CD11b+>Gr-1+. CD11b+Gr-1 high was considered as Granulocytic MDSC and CD11b+Gr-1 low was considered as monocytic MDSC. Data is shown as mean percentage±SD, n=5. *, $P<0.05$; , $P<0.01$; * $P<0.001$ (D) Effect of treatment on Treg in peripheral blood and spleen cells. CD4+CD25+ double positive of the T lymphocyte population was considered as Treg. Data is shown as mean percentage±SD, n=5, , $P<0.01$; * $P<0.001$. (E) Surface expression of PD1, CTLA4 and Tim-3 on T lymphocytes. Data shown as mean percentage of CD3+PD1+/CLTA4+/Tim-3+±SD, n=5; *, $P<0.05$; , $P<0.01$; * $P<0.001$. (F) Effect of treatments of TUSC2 and anti-PD1 are shown as ratio of NK/MDSC cells as well as CD8 T effector/Treg cells among peripheral blood leukocytes. Data shown as mean±SD, n=5, Statistical analysis of flow data was done by general linear regression models and CONTRAST statement in PROC GENMOD procedure in SAS. *, $P<0.05$; , $P<0.01$; * $P<0.001$

FIGS. 4A-4F: Dependence of the antitumor activity of TUSC2 on natural killer cells that generate a Th1-mediated immune response. The cytokines IL-15 and IL-18 were associated with natural killer cell regulation. (A) Depletion of NK cells abrogated treatment efficacy and the anti-tumor immune response. Tumor bioluminescence intensity graph shows the signals coming from tumor treated with TUSC2 and combination in NK depleted and non-depleted mice. NK1.1 antibody was injected every 3 days for 5 times for depletion of NK cells. The control group was treated with nanovesicles loaded with empty (no TUSC2 gene) vector. *, $P<0.05$; **, $P<0.01$. (B) Anti-tumor activity of TUSC2+anti-PD1 treatment was affected by CD8 T cells depletion shown in tumor intensity graph (n=5 mice/group). (C) 10 days after treatment, serum levels of IFN-γ and IL-4 cytokines in NK depleted and non-depleted mice were determined by luminex assay and the bars are shown as ratio of IFN-γ (Th1) and IL-4 (Th2). Data is shown as mean±SD, n=3. *, $P<0.05$, \*\*, P<0.01, \*\*\*, P<0.001, \*\*\*\*, P<0.0001 (D) Level of IL-18 and IL-15 cytokine changes after treatment in NK depleted and non-depleted mice. The Luminex assay was used to measure serum cytokines. Data is shown as mean pg/ml±SD, n=3. \*, P<0.05, \*\*, P<0.01, \*\*\*, P<0.001, \*\*\*\*, P<0.0001 (E) Fold expression of IL-15Ra and IL-18R1 in sorted NK cells from mice treated with TUSC2 as compared with control. Data is shown as mean±SD, n=3; \* P<0.05, \*\*, P<0.01 determined with multiple t-test. (F) NanoString analysis of tumors treated with TUSC2 and TUSC2+PD1 for comparing the fold change mRNA expression of IL-15Ra and IL-18R1.

FIGS. 5A-5I: Combined TUSC2 and anti-PD1 treatment significantly improved survival in a KRAS-mutant lung metastasis mouse model and recruited natural killer cells to tumor-bearing lungs. (A) 344SQ-luc cells were used for this experimental metastasis model which has KrasG12D allele and knock-in of a Trp53R172HAG allele. The PD-L1 expression level was determined by flow cytometry and compared with that of CMT167-luc cells. (B) Sequential treatment of checkpoint blockade (anti-PD1 and anti-CTLA4) and TUSC2 is shown schematically. (C) Survival is shown in Kaplan Meier curves after treatment. 344SQ cells were injected intravenously and mice were treated with TUSC2 and checkpoint blockade alone or in combination (shown in groups). The control group was treated with nanovesicles loaded with empty (no TUSC2 gene) vector and survival was recorded (n=10 mice/group). The Univariate Cox model was used for statistical analysis to compare the overall survival among treatment groups. The highest percent survival was seen in the TUSC2+PD1 group (left), followed by TUSC2, PD1 and control. Similarly, the highest percent survival was observed in the TUSC2+PD1+CTL4 group (right) followed by TUSC2, PD1+CTLA4, and control. (D) Bioluminescence images of tumor bearing mice taken by IVIS 200 showed lung specific colonization of tumor cells. The level of signal intensity is shown among treatment groups. A representative of three independent experiments is shown. (E) Dissected lung images shown the tumor nodule status two weeks after tumor implantation. (F) (G) (H) & (I) Single cells were prepared from metastasized lungs from different groups according to the protocol described in methods and CD49b+NK cells, CD4+CD25+ Treg, Gr-1+ MDSC and PD-L-1 and PD-L2 (+)ve leukocytes infiltration were determined by flow cytometry. Data were normalized based on per gram of tumor tissue. NK cells were gated from CD45+CD3-CD19-; MDSC were gated as follows: CD45+>CD3->MHCII low> CD11b+>GR-1+. PD+CT indicate anti-PD1 and anti-CTLA4 treatment. Data is shown as cells/gram of tissue±SD, n=5. \*, P<0.05, \*\*, P<0.01, \*\*\*, P<0.001. CONTRAST statement in PROC GENMOD procedure in SAS was used to compare the flow data for statistical analysis.

FIGS. 6A-6F: Combined TUSC2 and anti-PD1 treatment altered immune gene expression profiles in the tumor microenvironment. Gene expression analysis of a NanoString pan-cancer immune panel of 776 genes were performed for 12 samples (n=3/treatment group) from four treatment groups (empty vector nanovesicles, TUSC2, anti-PD1 and combination). Data generated by nCounter system is normalized prior to being used to quantify the gene profile and statistical analysis. The positive controls, housekeeping genes and negative controls are used to adjust for sample preparation variation, background noise and RNA content variation. Linear model is used to evaluate the overall treatment effect and contrast is used to make pairwise comparisons of interest. The resulting p values are modeled using the beta-uniform mixture (BUM) model to determine a false discovery rate (FDR) cutoff and identify significantly differentially expressed genes. (A) Heat map shows the overall significant genes among treatment groups. 33 genes were significantly changed with treatment. (B) Pair-wise comparison between TUSC2+anti-PD1 and anti-PD1 identified another set of 13 genes. Volcano plot shows the separation of genes upregulated and downregulated by treatments. Statistically significant genes are shown in colors. (C) Selected genes known for anti-tumor immune response were highly upregulated at least 2-fold in the combination treatment group as compared with the single agent treatment. (D), (E) & (F) show the fold changes of CD8, INF-γ & transcription factors (Tbx21, Gata3) expression respectively by TUSC2, anti-PD1 and combination treatments as compared with control. All gene expression data shown here were generated by NanoString technology.

FIG. 10: NanoString gene expression analysis in tumor microenvironment. Pair-wise comparison between PD1 and TUSC2+PD1 combination treatment showed 13 significantly altered genes. P-value and fold changes of all 13 genes were listed. Linear model is used to evaluate the overall treatment effect and contrast is used to make pairwise comparisons of interest. The resulting p values are modeled using the beta-uniform mixture (BUM) model to determine a false discovery rate (FDR) cutoff and identify significantly differentially expressed genes.

DESCRIPTION OF ILLUSTRATIVE EMBODIMENTS

Figure 1E:
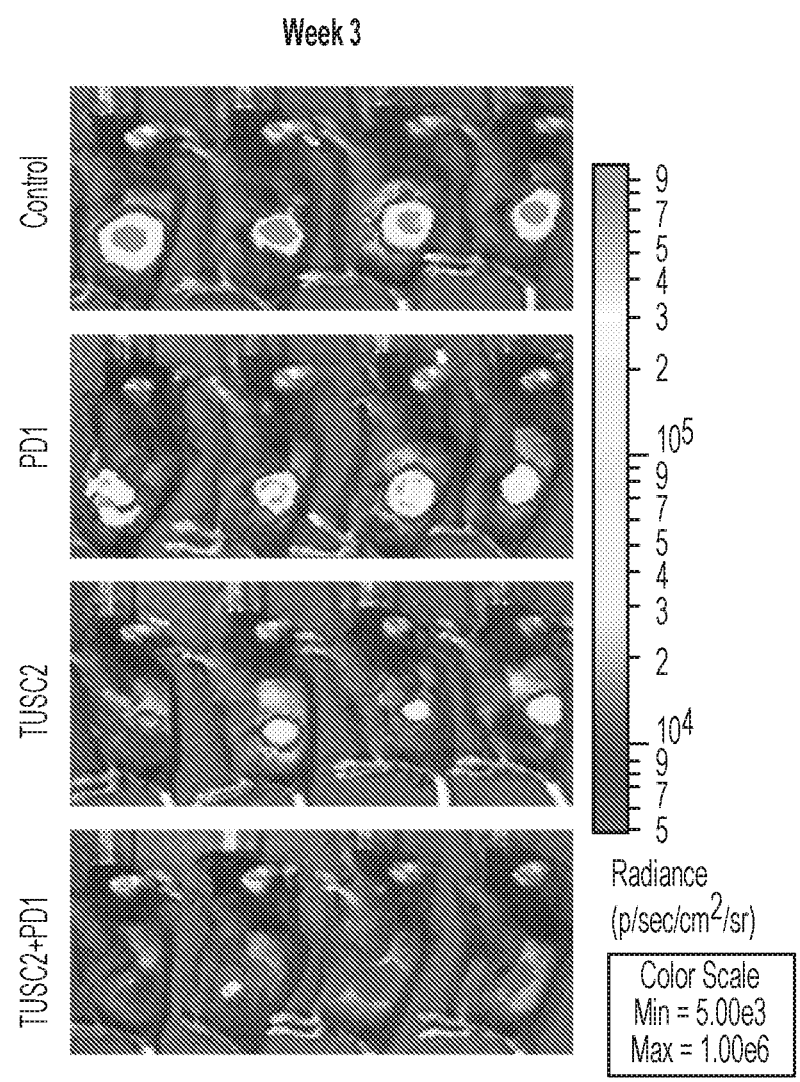

The development of cancer involves the deregulation of a number of cellular pathways that control normal cell growth. Healthy cells express a number of tumor suppressor genes, which act as molecular gatekeepers and prevent uncontrolled cell division. An important step in the development of a cancer cells, therefore, is disruption of tumor suppressor signaling pathways. In view of this, one promising avenue for cancer therapy involves expression of tumor suppressor genes in cancer cells to restore normal cellular growth controls. However, to date it was not known what types might act to enhance the efficacy of tumor suppressor therapies, such as TUSC2 therapy.

Studies in the instant patent application demonstrate for the first time that TUSC2 therapy is particularly effective when administered in conjunction with an immune checkpoint inhibitor. Immune checkpoint inhibitors, such as anti-PD1 therapies, operate by enhancing an individual's own immune cells to inhibit tumor growth. Conversely, therapeutic treatment of tumors with tumor suppressor agents, such as TUSC2 therapies is meant to reverse the transformed phenotype of the cancer cells. Since the later therapies would, if anything, render a tumor cell "less transformed" and possibly less immunogenic, it previously would have been counter intuitive to attempt to use TUSC2 therapies with immune checkpoint inhibitors. Nonetheless, the studies presented here demonstrate that anti-tumor efficacy an immune checkpoint inhibitor (e.g., anti-PD1 and/or CTLA4) is actually significantly enhanced when the therapy is combined with a TUSC2 therapy (see, e.g., FIG. 1).

Specifically, in the present studies, anti-PD1 showed limited efficacy in restraining tumor growth and extending survival in two Kras-mutant, G12V and G12D, syngeneic mouse models of lung adenocarcinoma with varying levels of PDL-1 expression. However, when combined with TUSC2 gene restoration, the impact on tumor regression and survival was far superior. TUSC2 altered both innate and adaptive immune cell populations. This was evidenced by significant increase in circulatory NK and CD8+ T cells and decrease of myeloid-derived suppressor cells (MDCS), regulatory T cells (Tregs), B cells, T cell checkpoint receptors PD1 and T-lymphocyte-associated protein 4 (CTLA-4), and mucin-domain containing-3 (TIM-3). The density of tumor-infiltrating NK and CD8+T cells was induced by the TUSC2-anti-PD1 combination. In vivo depletion of NK or CD8+T cells completely and partially mitigated efficacy of the combination, respectively, suggesting that while CD8+T cells might contribute to TUSC2-enhanced sensitivity to anti-PD1, NK cells are needed for this synergy. Cytokine levels of Interferon gamma (IFNγ), interleukins 15 and 18 (IL15 and IL18) were increased significantly after TUSC2 restoration, which also enhanced survival by the dual checkpoint blockade, anti-PD1+anti-CTLA-4. Gene expression profile analysis showed altered tumor microenvironment by TUSC2-anti-PD1 combined treatment. These data indicate that this novel combination therapy may be a potential strategy for treating Kras mutant lung adenocarcinoma.

Thus, the methods detailed herein provide for the first time effective methods for treating cancers by the combined use of immune checkpoint inhibitors and tumor suppressor agents (e.g., a TUSC2 therapy)

I. IMMUNE CHECKPOINT BLOCKADE

The term "immune checkpoint" refers to a component of the immune system which provides inhibitory signals to its components in order to regulate immune reactions. Known immune checkpoint proteins comprise CTLA-4, PD-1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012, *Nature Rev Cancer* 12:252-264; Mellman et al., 2011, *Nature* 480:480-489).

The term "PD-1 axis binding antagonist" refers to a molecule that inhibits the interaction of a PD-1 axis binding partner with either one or more of its binding partners, so as to remove T-cell dysfunction resulting from signaling on the PD-1 signaling axis—with a result being to restore or enhance T-cell function (e.g., proliferation, cytokine production, target cell killing). The term "PD-1" axis refers to any component of the PD-1 immune checkpoint (e.g., PD-1, PD-L1, and PD-L2). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1 and/or PD-L2. The PD-1 binding antagonist may be a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. An exemplary PD-1 binding antagonist is an anti-PD-1 antibody. For example the PD-1 binding antagonist is MDX-1106 (nivolumab), MK-3475 (pembrolizumab), CT-011 (pidilizumab), or AMP-224.

The term "PD-L1 binding antagonist" refers to a molecule that decreases, blocks, inhibits, abrogates or interferes with signal transduction resulting from the interaction of PD-L1 with either one or more of its binding partners, such as PD-1 or B7-1. For example, a PD-L1 binding antagonist is a molecule that inhibits the binding of PD-L1 to its binding partners. In a specific aspect, the PD-L1 binding antagonist inhibits binding of PD-L1 to PD-1 and/or B7-1. The PD-L1 binding antagonists may include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 or B7-1. For example, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In one example, a PD-L1 binding antagonist is an anti-PD-L1 antibody. The anti-PD-L1 antibody may be YW243.55.S70, MDX-1105, MPDL3280A, or MEDI4736.

The term "PD-L2 binding antagonist" refers to a molecule that decreases, blocks, inhibits, abrogates or interferes with signal transduction resulting from the interaction of PD-L2 with either one or more of its binding partners, such as PD-1. A PD-L2 binding antagonist may be a molecule that inhibits the binding of PD-L2 to one or more of its binding partners. For example, the PD-L2 binding antagonist inhibits binding of PD-L2 to PD-1, such as PD-L2 antagonists including anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1.

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

Thus, the present disclosure provides methods of enhancing the efficacy of immune checkpoint blockade by administration of a tumor suppressor agent, such as TUSC2 therapy. As discussed above, immune checkpoints either turn up a signal (e.g., co-stimulatory molecules) or turn down a signal. Inhibitory immune checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, antibodies, such as human antibodies (e.g., International Patent Publication No. WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example, it is known that lambrolizumab is also known under the alternative and equivalent names MK-3475 and pembrolizumab.

It is contemplated that any of the immune checkpoint inhibitors that are known in the art to stimulate immune responses may be used. This includes inhibitors that directly or indirectly stimulate or enhance antigen-specific T-lymphocytes. These immune checkpoint inhibitors include, without limitation, agents targeting immune checkpoint proteins and pathways involving PD-L2, LAG3, BTLA, B7H4 and TIM3. For example, LAG3 inhibitors known in the art include soluble LAG3 (IMP321, or LAG3-Ig disclosed in WO2009044273, incorporated herein by reference) as well as mouse or humanized antibodies blocking human LAG3 (e.g., IMP701 disclosed in WO2008132601, incorporated herein by reference), or fully human antibodies blocking human LAG3 (such as disclosed in EP 2320940, incorporated herein by reference). Another example is provided by the use of blocking agents towards BTLA, including without limitation antibodies blocking human BTLA interaction with its ligand (such as 4C7 disclosed in WO2011014438, incorporated herein by reference). Yet another example is provided by the use of agents neutralizing B7H4 including without limitation antibodies to human B7H4 (disclosed in WO 2013025779, and in WO2013067492, each incorporated herein by reference) or soluble recombinant forms of B7H4 (such as disclosed in US20120177645, incorporated herein by reference). Yet another example is provided by agents neutralizing B7-H3, including without limitation antibodies neutralizing human B7-H3 (e.g. MGA271 disclosed as BRCA84D and derivatives in US 20120294796, incorporated herein by reference). Yet another example is provided by agents targeting TIM3, including without limitation antibodies targeting human TIM3 (e.g. as disclosed in WO 2013006490 A2 or the anti-human TIM3, blocking antibody F38-2E2 disclosed by Jones et al., J Exp Med. 2008; 205(12):2763-79, each, incorporated herein by reference).

A. PD-1 Axis Antagonists

T cell dysfunction or anergy occurs concurrently with an induced and sustained expression of the inhibitory receptor, programmed death 1 polypeptide (PD-1). Thus, therapeutic targeting of PD-1 and other molecules which signal through interactions with PD-1, such as programmed death ligand 1 (PD-L1) and programmed death ligand 2 (PD-L2) is provided herein. PD-L1 is overexpressed in many cancers and is often associated with poor prognosis (Okazaki T et al., *Intern. Immun.* 2007 19(7):813). Thus, improved methods of treating cancer by inhibiting the PD-L1/PD-1 interaction in combination with administration of a tumor suppressor agent, such as a TUSC2 therapy.

For example, PD-1 axis binding antagonists include a PD-1 binding antagonist, a PDL1 binding antagonist and a PDL2 binding antagonist. Alternative names for "PD-1" include CD279 and SLEB2. Alternative names for "PDL" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 binding antagonists include Pidilizumab, also known as CT-011, MEDI0680, also known as AMP-514, and REGN2810.

In some embodiments, the immune checkpoint inhibitor is a PD-L1 antagonist such as Durvalumab, also known as MEDI4736, atezolizumab, also known as MPDL3280A, or avelumab, also known as MSB00010118C. In certain aspects, the immune checkpoint inhibitor is a PD-L2 antagonist such as rHIgM12B7. In some aspects, the immune checkpoint inhibitor is a LAG-3 antagonist such as, but not limited to, IMP321, and BMS-986016. The immune checkpoint inhibitor may be an adenosine A2a receptor (A2aR) antagonist such as PBF-509.

In some embodiments, the antibody described herein (such as an anti-PD-1 antibody, an anti-PDL1 antibody, or an anti-PDL2 antibody) further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation.

Accordingly, an antibody used herein can be aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxy amino acid, most commonly serine or threonine, although 5-hydroxyproline or 5-hydroxy lysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

The antibody or antigen binding fragment thereof, may be made using methods known in the art, for example, by a process comprising culturing a host cell containing nucleic acid encoding any of the previously described anti-PDL1, anti-PD-1, or anti-PDL2 antibodies or antigen-binding fragment in a form suitable for expression, under conditions suitable to produce such antibody or fragment, and recovering the antibody or fragment.

B. CTLA-4

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include soluble CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

C. Killer Immunoglobulin-Like Receptor (KIR)

Another immune checkpoint inhibitor for use in the present disclosure is an anti-KIR antibody. Anti-human-KIR antibodies (or VH/VL domains derived therefrom) suitable for use in the present methods can be generated using methods well known in the art.

Alternatively, art recognized anti-KIR antibodies can be used. The anti-KIR antibody can be cross-reactive with multiple inhibitory KIR receptors and potentiates the cytotoxicity of NK cells bearing one or more of these receptors. For example, the anti-KIR antibody may bind to each of KIR2D2DL1, KIR2DL2, and KIR2DL3, and potentiate NK cell activity by reducing, neutralizing and/or reversing inhibition of NK cell cytotoxicity mediated by any or all of these KIRs. In some aspects, the anti-KIR antibody does not bind KIR2DS4 and/or KIR2DS3. For example, monoclonal antibodies 1-7F9 (also known as IPH2101), 14F1, 1-6F1 and 1-6F5, described in WO 2006/003179, the teachings of which are hereby incorporated by reference, can be used.

Antibodies that compete with any of these art-recognized antibodies for binding to KIR also can be used. Additional art-recognized anti-KIR antibodies which can be used include, for example, those disclosed in WO 2005/003168, WO 2005/009465, WO 2006/072625, WO 2006/072626, WO 2007/042573, WO 2008/084106, WO 2010/065939, WO 2012/071411 and WO 2012/160448, all incorporated herein by reference.

An exemplary anti-KIR antibody is lirilumab (also referred to as BMS-986015 or IPH2102). In other embodiments, the anti-KIR antibody comprises the heavy and light chain complementarity determining regions (CDRs) or variable regions (VRs) of lirilumab. Accordingly, in one embodiment, the antibody comprises the CDR1, CDR2, and CDR3 domains of the heavy chain variable (VH) region of lirilumab, and the CDR1, CDR2 and CDR3 domains of the light chain variable (VL) region of lirilumab. In another embodiment, the antibody has at least about 90% variable region amino acid sequence identity with lirilumab.

II. TUMOR SUPPRESSOR THERAPIES

In certain aspects, concerns compositions and methods for delivering a nucleic acid or a polypeptide to a cell. In particular, provided herein are nanoparticle-nucleic acid or nanoparticle-polypeptide complexes and methods of administering such complexes to a subject. The complexes comprise a TUSC2 polypeptide and/or nucleic acid in association with a nanoparticle. As used herein, "association" means a physical association, a chemical association or both. For example, an association can involve a covalent bond, a hydrophobic interaction, encapsulation, surface adsorption, or the like.

Polypeptides and nucleic acids typically have difficulty crossing cellular membranes. Both types of molecules include charged residues, which hinder membrane binding and membrane transport into cells. The present embodiments overcome this difficulty by, providing nanoparticle complexes that facilitate cellular uptake.

In accordance with the present embodiments, a polypeptide and/or nucleic acid may be associated with a nanoparticle to form nanoparticle complex. In some embodiments, the nanoparticle is a liposomes or other lipid-based nanoparticle such as a lipid-based vesicle (e.g., a DOTAP:cholesterol vesicle). As used in cancer therapy, liposomes take advantage of the increased fenestrations in the cancer neovasculature to enhance liposome concentration at tumor sites.

In other embodiments, the nanoparticle is a non-lipid nanoparticle, such as an iron-oxide based superparamagnetic nanoparticles. Superparamagnetic nanoparticles ranging in diameter from about 10 to 100 nm are small enough to avoid sequestering by the spleen, but large enough to avoid clearance by the liver. Particles this size can penetrate very small capillaries and can be effectively distributed in body tissues. Superparamagnetic nanoparticles complexes can be used as MRI contrast agents to identify and follow those cells that take up the therapeutic complexes. In certain embodiments, the nanoparticle is a semiconductor nanocrystal or a semiconductor quantum dot, both of which can be used in optical imaging. In further embodiments, the nanoparticle can be a nanoshell, which comprises a gold layer over a core of silica. One advantage of nanoshells is that a polypeptideor nucleic acid can be conjugated to the gold layer using standard chemistry. In other embodiments, the nanoparticle can be a fullerene or a nanotube (Gupta et al., 2005).

In accordance with the present embodiments, nanoparticle complexes can be targeted to specific tissues and cells. This can be accomplished by conjugating a cell targeting moiety to the nanoparticle. The targeting moiety can be, but is not limited to, a protein, peptide, lipid, steroid, sugar, carbohydrate or synthetic compound. Cell targeting moieties such as ligands recognize and bind to their cognate receptors on the surface of cells. Similarly, antibody can act as cell targeting moieties by recognizing their cognate antigens on the cell surface. In certain embodiments, targeted nanoparticle complexes provided herein can enhance the specificity of disease treatment and increase the amount of therapeutic agent entering a targeted cell.

A. Nanoparticles

As used herein, the term "nanoparticle" refers to any material having dimensions in the 1-1,000 nm range. In some embodiments, nanoparticles have dimensions in the 50-500 nm range. Nanoparticles used in the present embodiments include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube (Ferrari, 2005). The conjugation of polypeptide or nucleic acids to nanoparticles provides structures with potential application for targeted delivery, controlled release, enhanced cellular uptake and intracellular trafficking, and molecular imaging of therapeutic peptides in vitro and in vivo (West, 2004; Stayton et al., 2000; Ballou et al., 2004; Frangioni, 2003; Dubertret et al., 2002; Michalet et al., 2005; Dwarakanath et al., 2004.

1. Lipid-Based Nanoparticles

Lipid-based nanoparticles include liposomes, lipid preparations and lipid-based vesicles (e.g., DOTAP:cholesterol vesicles). Lipid-based nanoparticles may be positively charged, negatively charged or neutral. In certain embodiments, the lipid-based nanoparticle is neutrally charged (e.g., a DOPC liposome).

A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Liposomes provided herein include unilamellar liposomes, multilamellar liposomes and multivesicular liposomes. Liposomes provided herein may be positively charged, negatively charged or neutrally charged. In certain embodiments, the liposomes are neutral in charge.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In specific aspects, a polypeptide or nucleic acids may be, for example, encapsulated in the aqueous interior of a liposome, interspersed within the lipid bilayer of a liposome, attached to a liposome via a linking molecule that is associated with both the liposome and the polypeptide/nucleic acid, entrapped in a liposome, complexed with a liposome, or the like.

A liposome used according to the present embodiments can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with a polypeptide, nucleic acid, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

The dried lipids or lyophilized liposomes prepared as described above may be dehydrated and reconstituted in a solution of a protein or peptide and diluted to an appropriate concentration with a suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

In other alternative methods, liposomes can be prepared in accordance with other known laboratory procedures (e.g., see Bangham et al., 1965; Gregoriadis, 1979; Deamer and Uster, 1983; Szoka and Papahadjopoulos, 1978, each incorporated herein by reference in relevant part). Additional liposomes which may be useful with the present embodiments include cationic liposomes, for example, as described in WO02/100435A1, U.S. Pat. No. 5,962,016, U.S. Application 2004/0208921, WO03/015757A1, WO04029213A2, U.S. Pat. Nos. 5,030,453, and 6,680,068, all of which are hereby incorporated by reference in their entirety without disclaimer. A process of making liposomes is also described in WO04/002453A1. Neutral lipids can be incorporated into cationic liposomes (e.g., Farhood et al., 1995). Various neutral liposomes which may be used in certain embodiments are disclosed in U.S. Pat. No. 5,855,911, which is incorporated herein by reference. These methods differ in their respective abilities to entrap aqueous material and their respective aqueous space-to-lipid ratios.

The size of a liposome varies depending on the method of synthesis. Liposomes in the present embodiments can be a variety of sizes. In certain embodiments, the liposomes are small, e.g., less than about 100 nm, about 90 nm, about 80 nm, about 70 nm, about 60 nm, or less than about 50 nm in external diameter. For example, in general, prior to the incorporation of nucleic acid, a DOTAP:cholesterol liposome for use according to the present embodiments comprises a size of about 50 to 500 nm. Such liposome formulations may also be defined by particle charge (zeta potential) and/or optical density (OD). For instance, a DOTAP:cholesterol liposome formulation will typically comprise an $OD_{400}$ of less than 0.45 prior to nucleic acid incorporation. Likewise, the overall charge of such particles in solution can be defined by a zeta potential of about 50-80 mV.

In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

In certain embodiments, the lipid based nanoparticle is a neutral liposome (e.g., a DOPC liposome). "Neutral liposomes" or "non-charged liposomes", as used herein, are defined as liposomes having one or more lipid components that yield an essentially-neutral, net charge (substantially non-charged). By "essentially neutral" or "essentially non-charged", it is meant that few, if any, lipid components within a given population (e.g., a population of liposomes) include a charge that is not canceled by an opposite charge of another component (i.e., fewer than 10% of components include a non-canceled charge, more preferably fewer than 5%, and most preferably fewer than 1%). In certain embodiments, neutral liposomes may include mostly lipids and/or phospholipids that are themselves neutral under physiological conditions (i.e., at about pH 7).

Liposomes and/or lipid-based nanoparticles of the present embodiments may comprise a phospholipid. In certain embodiments, a single kind of phospholipid may be used in the creation of liposomes (e.g., a neutral phospholipid, such as DOPC, may be used to generate neutral liposomes). In other embodiments, more than one kind of phospholipid may be used to create liposomes.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes. In certain embodiments, a lipid that is not a phospholipid (e.g., a cholesterol) may be used Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used, in certain embodiments, as the primary phosphatide (i.e., constituting 50% or more of the total phosphatide composition) because this may result in instability and leakiness of the resulting liposomes.

2. DOTAP:Cholesterol Nanoparticle

In certain embodiments, the lipid-based vesicle is a DOTAP:cholesterol nanoparticle. DOTAP:cholesterol nanoparticles are prepared by mixing the cationic lipid DOTAP (1,2-bis(oleoyloxy)-3-(trimethylammonio)-propane) with cholesterol. Vesicles prepared with DNA can form a structure (called a "sandwich") where the DNA appears to be condensed between two lipid bilayers (U.S. Pat. Nos. 6,770, 291 and 6,413,544).

A DOTAP:cholesterol-nucleic acid complex can be prepared as in the following non-limiting example. The DOTAP:cholesterol (DC) nanoparticles (sized 50 to 500 nm) are synthesized as described previously (U.S. Pat. Nos. 6,770, 291 and 6,413,544; Templeton, 1997). Briefly, 420 mg of DOTAP and 208 mg of cholesterol are measure and mixed together with 30 ml of chloroform. Mixture is then allowed to dry on a rotary evaporator for 30 minutes and freeze dry for 15 minutes. The dried mixture is reconstituted in 30 ml of D5W by swirling at 50° C. for 45 minutes and 37° C. for 10 minutes. The mixture is ten subjected to low frequency sonication for five minutes to form liposomes. DOTAP:cholesterol liposome are then heated to 50° C. and sequentially filtered through 1.0, 0.45, 0.2 and 0.1 m sterile Whatman filters. The synthesized nanoparticles are stored at 4° C. and used for preparing nanoparticle complexes. The formulated DOTAP:cholesterol liposome should be evenly dispersed with a particle size of 50-250 nm, an $OD_{400}$ of less than 0.45 and zeta potential of 50-80 mV. Residual $CHCl_3$ levels should be less than 60 ppm.

To prepare DOTAP:cholesterol-nucleic acid nanoparticles, 240 µl of liposomes (see above) are diluted in 360 µl D5W at room temperature. DNA (~5 mg/ml) is added to the mixture to a total volume of 600 al. The mixture is moved up and down in a pipet to mix. Once settled the mixture should have an $OD_{400}$ of between 0.65 and 0.95, a particle size of 200-500 nm and be confirmed gram stain negative. The liposome complexes are stored at between 3° C. and 28° C. and agitated as little as possible.

B. Targeting of Nanoparticles

Targeted delivery is achieved by the addition of ligands without compromising the ability of nanoparticles to deliver their payloads. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-α, nerve growth factor, albumin, HIV Tat peptide, RGD peptide, and insulin, as well as others (Gupta et al., 2005; Ferrari, 2005).

C. TUSC2 Expression Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

In certain embodiments, provided herein is the use of nucleic acids TUSC2 coding sequence. For example, such vector can be used for recombinant production of a TUSC2 polypeptide and/or for the expression of TUSC2 in vivo in a subject. The sequences may be modified, given the ability of several different codons to encode a single amino acid, while still encoding for the same protein or polypeptide. Optimization of codon selection can also be undertaken in light of the particular organism used for recombinant expression or may be optimized for maximal expression in human cell (e.g., a cancer cell). Vector for use in accordance with the present embodiments additionally comprise elements that control gene expression and/or aid in vector production and purification.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the coding nucleic acid segment under the control of a recombinant, exogenous or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include viral promoter and enhancers such as the CMV promoter.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

2. Translation Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference). Inclusion of such splice sites also can enhance expression by averting non-sense mediated decay of resulting RNA transcripts.

5. Termination Signals

The vectors or constructs of the present embodiments will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

Terminators contemplated for use in the present embodiments include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the present embodiments, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

8. Selectable and Screenable Markers

In certain embodiments, cells containing a nucleic acid construct provided herein may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of 2-24 hr, the cells are collected by centrifugation and washed to remove residual media.

10. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Viruses may thus be utilized that encode and express TUSC2. Non-limiting examples of virus vectors that may be used to deliver a TUSC2 nucleic acid are described below.

Adenoviral Vectors.

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

AAV Vectors.

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors. Retroviruses have the ability to integrate their genes into the host genome, transferring a large amount of foreign genetic material, infecting a broad spectrum of species and cell types and of being packaged in special cell-lines (Miller, 1992). In order to construct a retroviral vector, a nucleic acid (e.g., one encoding a protein of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif vpr, vpu and nef are deleted making the vector biologically safe.

Other Viral Vectors.

Other viral vectors may be employed as vaccine constructs in the present embodiments. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Modified Viruses. A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

III. PHARMACEUTICAL FORMULATIONS

Pharmaceutical compositions provided herein comprise an effective amount of one or more TUSC2 therapeutic and/or an immune checkpoint inhibitor and, optionally, an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least TUSC2 nucleic acid, peptide or a nanoparticle complex or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

In certain embodiments, the pharmaceutical composition may comprise different types of carriers depending on whether it is to be administered in solid, liquid or aerosol form, and whether it need to be sterile for such routes of administration as injection. In certain embodiments, pharmaceutical compositions provided herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

In certain embodiments, the pharmaceutical composition is administered intraperitoneally. In further embodiments, the pharmaceutical composition is administered intraperitoneally to treat a cancer (e.g., a cancerous tumor). For example, the pharmaceutical composition may be administered intraperitoneally to treat gastrointestinal cancer. In certain embodiments it may be desirable to administer the pharmaceutical composition into or near a tumor.

In certain preferred embodiments, the pharmaceutical composition is administered orally to treat a cancer (e.g., a gastrointestinal cancer).

In certain embodiments, the actual dosage amount of a composition administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 15 microgram/kg/body weight, about 20 microgram/kg/body weight, about 25 microgram/kg/body weight, about 30 microgram/kg/body weight, about 35 microgram/kg/body weight, about 0.04 milligram/kg/body weight, about 0.05 milligram/kg/body weight, about 0.06 milligram/kg/body weight, about 0.07 milligram/kg/body weight, about 0.08 milligram/kg/body weight, about 0.09 milligram/kg/body weight, about 0.1 milligram/kg/body weight, about 0.2 milligram/kg/body weight, to about 0.5 mg/kg/body weight or more per administration, and any range derivable therein. In non-limiting examples of a derivable range from the numbers listed herein, a range of about 0.01 mg/kg/body weight to about 0.1 mg/kg/body weight, about 0.04 microgram/kg/body weight to about 0.08 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The one or more peptides, nanoparticle complexes or additional agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present embodiments. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the one or more polypeptide, nucleic acid or nanoparticle complexes are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

Treatment with the anti-cancer peptide or nanoparticle-complex may precede or follow the other agent treatment by intervals ranging from minutes to weeks. In embodiments where the other agent and the anti-cancer peptide or nanoparticle complex are applied separately to the cell, one would generally ensure that a significant period of time did not expire between the time of each delivery, such that the agent and the anti-cancer peptide or nanoparticle complex would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Likewise, in certain aspects a TUSC2 therapy is administered in conjunction with an immune checkpoint inhibitor. Various combinations may be employed, where the TUSC2 therapy is "A" and the immune checkpoint inhibitor, is "B":

| A/B/A   | B/A/B | B/B/A | A/A/B | A/B/B | B/A/A | A/B/B/B | B/A/B/B |
|---------|-------|-------|-------|-------|-------|---------|---------|
| B/B/B/A |   B/B/A/B   | A/A/B/B | A/B/A/B | A/B/B/A | B/B/A/A |
| B/A/B/A |   B/A/A/B   | A/A/A/B | B/A/A/A | A/B/A/A | A/A/B/A |

In particular embodiments, prolonged absorption of an injectable composition can be brought about by the use in the compositions of agents delaying absorption, such as, for example, aluminum monostearate, gelatin or combinations thereof.

IV. COMBINATION THERAPIES

In order to increase the effectiveness of a nucleic acid, polypeptide or nanoparticle complex of the present embodiments, it may be desirable to combine these compositions with other agents effective in the treatment of the disease of interest.

As a non-limiting example, the treatment of cancer may be implemented with TUSC2 therapeutic and/or an immune checkpoint inhibitor of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the anti-cancer peptide or nanoparticle complex and the other includes the second agent(s). In particular embodiments, an anti-cancer peptide can be one agent, and an anti-cancer nanoparticle complex can be the other agent.

In certain embodiments, administration of the TUSC2 therapy and/or an immune checkpoint inhibitor of the present embodiments to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

a. Chemotherapy

Cancer therapies also include a variety of combination therapies. In some aspects a TUSC2 therapeutic and/or an immune checkpoint inhibitor of the embodiments is administered (or formulated) in conjunction with a chemotherapeutic agent. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a TUSC2 therapy of the present embodiments. The general approach for combined therapy is discussed below. Generally, the tumor cell must bear some marker that is amenable to targeting, i.e., is not present on the majority of other cells. Many tumor markers exist and any of these may be suitable for targeting in the context of the present embodiments. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid-based vectors such as liposomes or DOTAP:cholesterol vesicles. All of these methods are well known in the art (see, e.g. Sambrook et al., 1989; Ausubel et al., 1998; Ausubel, 1996).

Delivery of a vector encoding one of the following gene products will have a combined anti-hyperproliferative effect on target tissues. A variety of proteins are encompassed within the present embodiments, some of which are described below.

i. Inhibitors of Cellular Proliferation

As noted above, the tumor suppressor oncogenes function to inhibit excessive cellular proliferation. The inactivation of these genes destroys their inhibitory activity, resulting in unregulated proliferation.

Genes that may be employed as secondary treatment in accordance with the present embodiments include p53, p16, Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors), MCC and other genes listed in Table IV.

ii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, *Proc. Nat'l. Acad. Sci. USA*, 82(21):7439-43, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Anti-Inflammatory Agents

In certain aspects TUSC2 therapies and/or an immune checkpoint inhibitor are administered in conjuction with an anti-inflammatory agent. An anti-inflammatory agent is defined herein to refer to an agent that is known or suspected to be of benefit in the treatment or prevention of inflammation in a subject. Corticosteroids are a major class of anti-inflammatory agent. The corticosteroids may be short, medium, or long acting, and may be delivered in a variety of methods. A non-limiting list of corticosteroids contemplated in the present embodiments include the oral corticosteroids such as: cortisone, hydrocortisone, prednisone, and dexamethasone.

Another major class of anti-inflammatory agents are non-steroidal anti-inflammatory agents. Non-steroidal anti-inflammatory agents include a class of drugs used in the treatment of inflammation and pain. The exact mode of action of this class of drugs is unknown. Examples of members of this class of agents include, but are not limited to, ibuprofen, ketoprofen, flurbiprofen, nabumetone, piroxicam, naproxen, diclofenac, indomethacin, sulindac, tolmetin, etodolac, flufenamic acid, diflunisal, oxaprozin, rofecoxib, and celecoxib. One of ordinary skill in the art would be familiar with these agents. Included in this category are salicylates and derivates of salicylates, such as acetyl salicylic acid, sodium salicylate, choline salicylate, choline magnesium salicylate and diflunisal.

Other anti-inflammatory agents include anti-rheumatic agents, such as gold salts (e.g., gold sodium thiomalate, aurothioglucose, and auranofin), anti-rheumatic agents (e.g., chloroquine, hydroxychloroquine, and penicillamine), antihistamines (e.g., diphenhydramine, chlorpheniramine, clemastine, hydroxyzine, and triprolidine), and immunosuppressive agents (e.g., methotrexate, mechlorethamine, cyclophosphamide, chlorambucil, cyclosporine, and azathioprine). Other immunosuppressive agent contemplated by the present embodiments is tacrolimus and everolimus. Tacrolimus suppresses interleukin-2 production associated with T-cell activation, inhibits differentiation and proliferation of cytotoxic T cells. Today, it is recognized worldwide as the cornerstone of immunosuppressant therapy. One of ordinary skill in the art would be familiar with these agents, and other members of this class of agents, as well as the mechanism of actions of these agents and indications for use of these agents.

g. Other Agents

It is contemplated that other agents may be used in combination with the compositions provided herein to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the compositions provided herein by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the compositions provided herein to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the compositions provided herein to improve the treatment efficacy.

In certain embodiments, hormonal therapy may also be used in conjunction with the present embodiments or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—TUSC2 Therapy in Combination with Immune Checkpoint Inhibitor

Combination Treatment with TUSC2 and Anti-PD1 Effectively Inhibits Tumor Growth in G12V Kras-Mutant Syngeneic Lung Subcutaneous Model:

The murine lung carcinoma cell line CMT/167-luciferase with a Kras G12V mutation and a low level of TUSC2 expression was implanted subcutaneously in C57BL/6 mice. Ten mice were allocated to each groups: DOTAP: cholesterol (DC)-empty vector/Isotype; anti-PD1 antibody; DC-TUSC2 nanoparticles; and DC-TUSC2 nanoparticles+anti-PD1 antibody. The sequential treatments of TUSC2 (i.v.) and anti-PD1 (i.p.) which were randomized are shown in FIG. 1A. There was no toxicity associated with the combination treatment. Tumor volumes and bioluminescence intensities were measured with a caliper and IVIS imaging, respectively. Expression of PD-L1 in CMT/167 cells is 23.7% (FIG. 1B). Anti-PD1 showed limited efficacy to restrain tumor growth, whereas TUSC2 inhibited tumor growth significantly (FIG. 1C). The combination further enhanced tumor regression by TUSC2. The mean volumes for isotype control, anti-PD1, TUSC2, and TUSC2+anti-PD1 were 800 mm$^3$, 600 mm$^3$, 300 mm$^3$, and 180 mm$^3$, respectively (*$p<0.05$; $p<0.01$; and *$p<0.001$). IVS imaging measuring bioluminescence intensity in tumors as total flux per second also show efficacy of the combination (FIGS. 1D-E). The posterior probability of a cooperative effect between TUSC2 and anti-PD1 was greater than 99%. These results suggest that in this model, TUSC2 synergizes with anti-PD1 in reducing tumor growth.

Figure 2A:
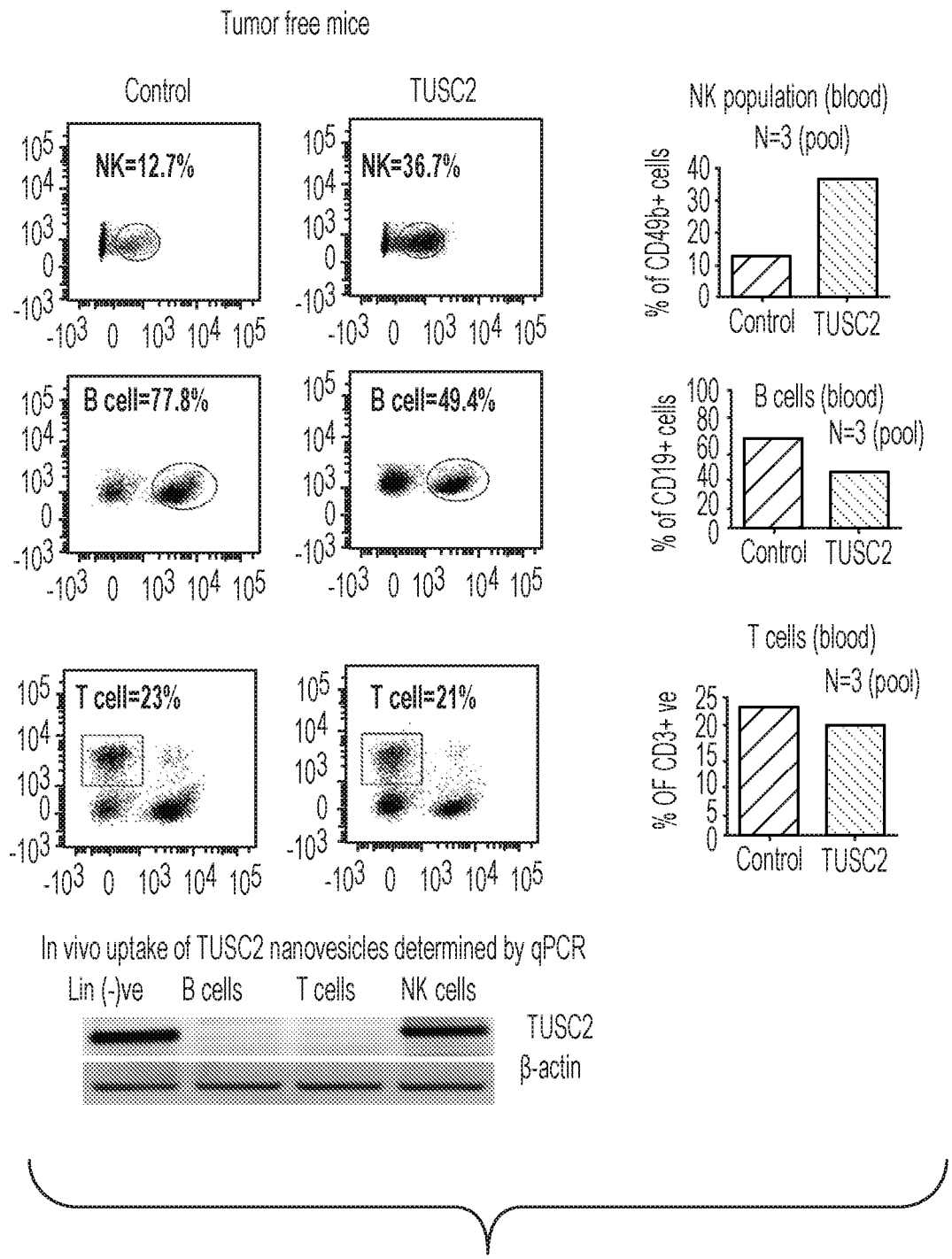
Figure 2B:
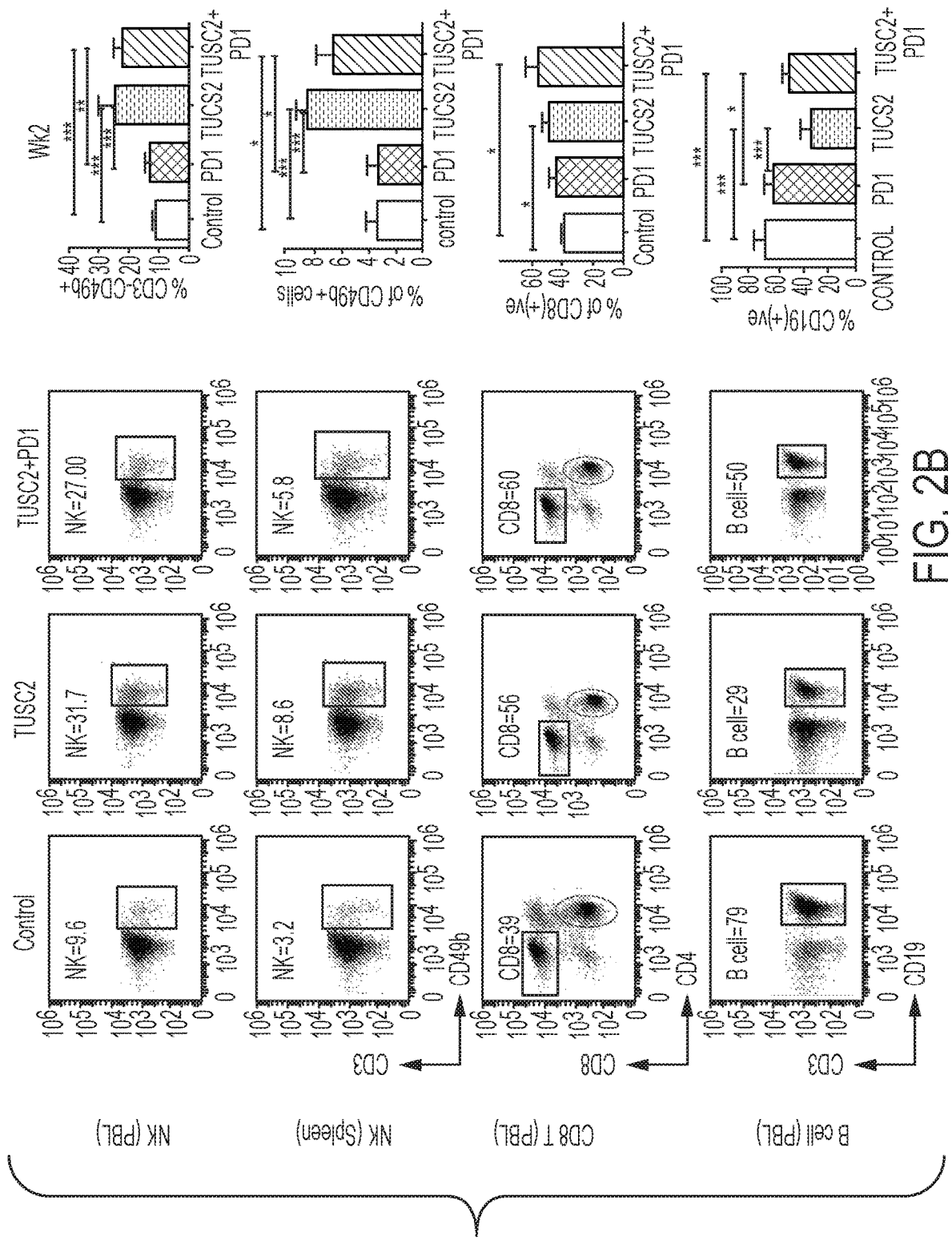

Combination Treatment with TUSC2 and Anti-PD1 Increases Density of NK and CD8$^+$ T Cells and Suppresses Regulatory Cells:

To delineate the immune impact of TUSC2 combination with anti-PD1, the major immune populations in peripheral blood leukocytes (PBLs) and splenocytes were profiled using ten color panel flow cytometry. The effect of intravenous delivery of TUSC2 nanovesicles on peripheral NK, B, and T cells in tumor free mice is shown in FIG. 2A. There was no difference between TUSC2 and TUSC2 plus anti-PD1 in tumor free mice. Gating strategy for flow cytometry analysis is shown in FIG. 1 supplement. After tumor cell inoculation, it was found that TUSC2 markedly and moderately induced the densities of NK and CD8$^+$T cells, respectively ($p<0.001$ and $p<0.05$), with pronounced concomitant decrease in B cells, MDSCs, Tregs, T cells expressing PD1, CTLA4, and Tim3 (FIGS. 2B-E). Anti-PD1 had no apparent effect on NK, T, and B cells, but decreased MDSCs, Tregs, and T cells expressing PD1, CTLA4, and Tim3. The combination treatment had the same effect as TUSC2 alone. The greatest difference in combination treatment was in enhancing the ratio of NK cells relative to MDSCs and CD8$^+$T cells relative to Tregs ($p<0.001$) (FIG. 2F). Taken together, these results indicate TUSC2-anti-PD1 synergy is likely associated with increased expansion of NK and CD8$^+$T cells.

Figure 3A:
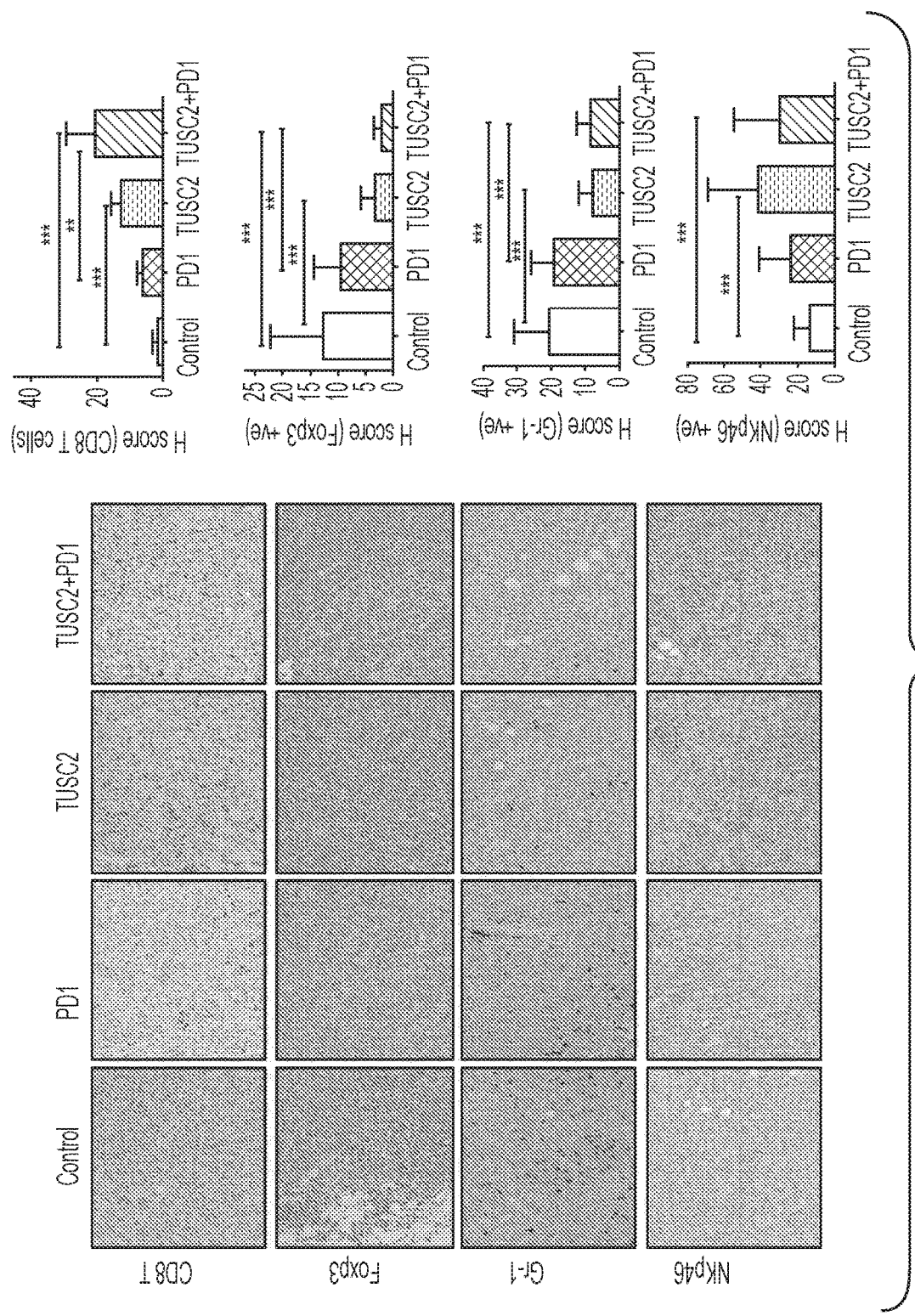
FIGS. 3A-3C: TUSC2 combination with anti-PD1 increased infiltration of NK and CD8 T cells and impeded infiltration of MDSC and Treg. (A) Subcutaneous tumors were treated with nanovesicles loaded with empty (no TUSC2 gene) vector (control), TUSC2 nanovesicles, anti-PD1 and TUSC2+anti-PD1. Formalin fixed resected tumors were immune stained with anti-CD8, anti-NKp46 for activated NK cells, anti-Gr-1 for MDSC, anti-Foxp3 for Treg. Vectra automated imaging system was employed to take high resolution images (20x) with imaging of 25% of the tumor area. N=5 tumor sections/groups were imaged. Approximately 100 images per treatment group were analyzed by InForm software for H-Scoring. Generalized linear regression models were used for statistical analysis of H scores among treatment groups. A compound symmetry covariance structure was used to account for inter-mouse variability and the repeated measure nature of the data. ESTIMATE statement in PROC MIXED procedure in SAS was used to compare the H scores between each pair of the treatment groups. *, $P<0.05$; , $P<0.01$; * $P<0.001$. (B) RNA was extracted from freshly resected tumors from treatment groups (n=3 tumors/treatment group) and gene expression of chemokines were determined by NanoString technology. Data were normalized and fold change of expression were analyzed by nCounter analysis software. Fold change were compared with control samples. Bar shows the average fold change (n=3). (C) Level of CCL4 and CCL5 chemokines in serum induced by TUSC2 treatment are shown. Subcutaneous tumor bearing mice were treated with TUSC2 according to the protocol described in method. Serum was collected 10 days after treatment and luminex multiplex ELISA were performed. Linear regression models were used to compare the chemokines between the treatment groups. ESTIMATE statement in PROC MIXED procedure in SAS was used to compare the chemokines between each pair of the treatment groups. SAS version 9.4 and S-Plus version 8.04 are used to carry out the computations for all analyses. Data; Mean±SD; N=3; ***, $P<0.001$.

Combination treatment with TUSC2 and anti-PD1 enhances tumor-infiltrating NK and CD$^+$8T cells:

To determine whether TUSC2+ anti-PD1 treatment is associated with denser tumor immune-cell infiltration, immune infiltrates were analyzed using Vectra high-throughput pathology system covering 25% of each tumor's area (N=5 tumors per treatment group). The entire subcutaneous tumors were uniformly resected for processing and several sections from each tumor were analyzed to eliminate any potential sampling bias considering varying tumor sizes between different treatment groups. H-score values were used taking into consideration the staining intensity in conjunction with the percentage of positive cells. When compared to control or anti-PD1, the combination increased CD8$^+$T cell density within tumors by 10 and 3 folds, respectively ($p<0.0001$; FIG. 3A). CD8$^+$T infiltrates in TUSC2 group were lower than those of the combination, although not significantly. Infiltration of activated NK cells, was highest in tumors treated with TUSC2 ($p<0.0001$) followed by the combination ($p<0.0001$) (FIG. 3A). Anti-PD1 increased NK infiltrates slightly, as compared to TUSC2 or the combination. Conversely, TUSC2 and TUSC2+anti-PD1 significantly suppressed tumor-infiltrated Foxp3 positive T cells ($p<0.0001$), a marker expressed by Tregs, and MDSCs bearing the tumor-suppressive granulocytic marker 1 (Gr-1) ($p<0.0001$). While anti-PD1 decreased Foxp3 density slightly ($p=0.18$), it had no effect on GR1. These results suggest that TUSC2 and the combination altered the tumor immune microenvironment.

Figure 3C:
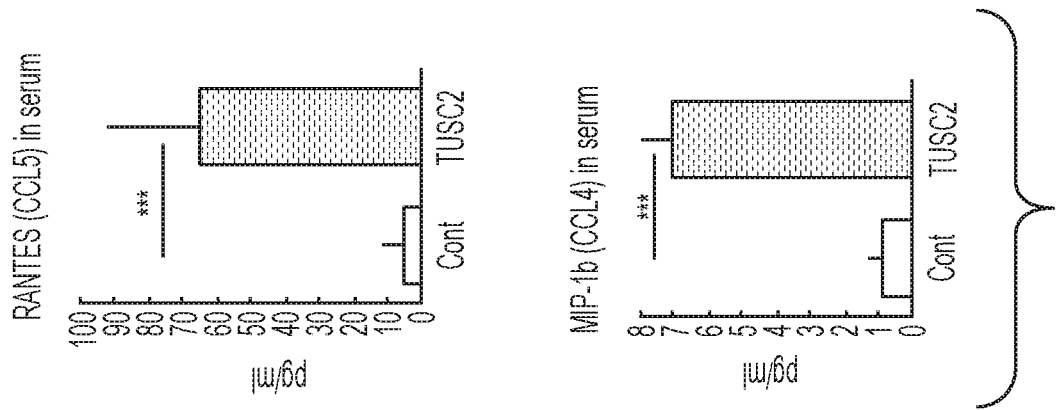
Figure 3B:
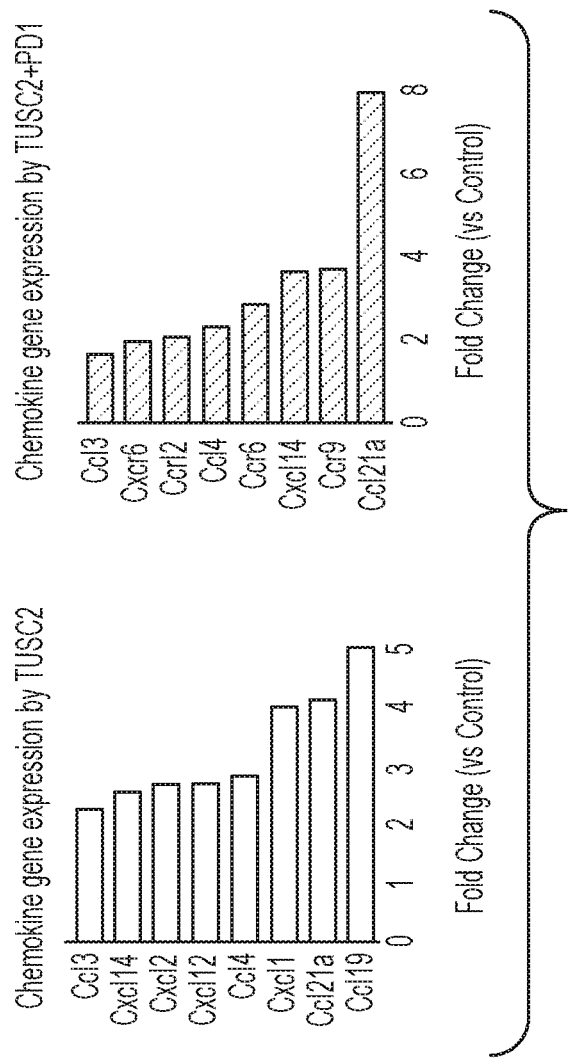

Combination Treatment with TUSC2 and Anti-PD1 Enhanced Chemokine Expression Associated with NK Cells and T Lymphocytes:

The expression profile of serum chemokines was analyzed using Nanostring technology. An upregulation of a set of chemokine genes was found that are associated with migration of T lymphocytes and NK cells after exposure to TUSC2 and the combination (FIG. 3B). Expression of CcL3 and CcL4, which are involved in NK cell migration via CCR5 recognition, more than doubled, whereas CcL21a and CcL19, which interact with CCR7 receptors and recruit T cells and dendritic cells to tumors (Viola et al., 2012; Griffith et al., 2014), increased by more than four folds compared to untreated controls. CcL4 and CcL5 serum chemokine levels were also increased by TUSC2 and TUSC2+anti-PD1 treatment as compared with the control group (FIG. 3C).

Figure 8A:
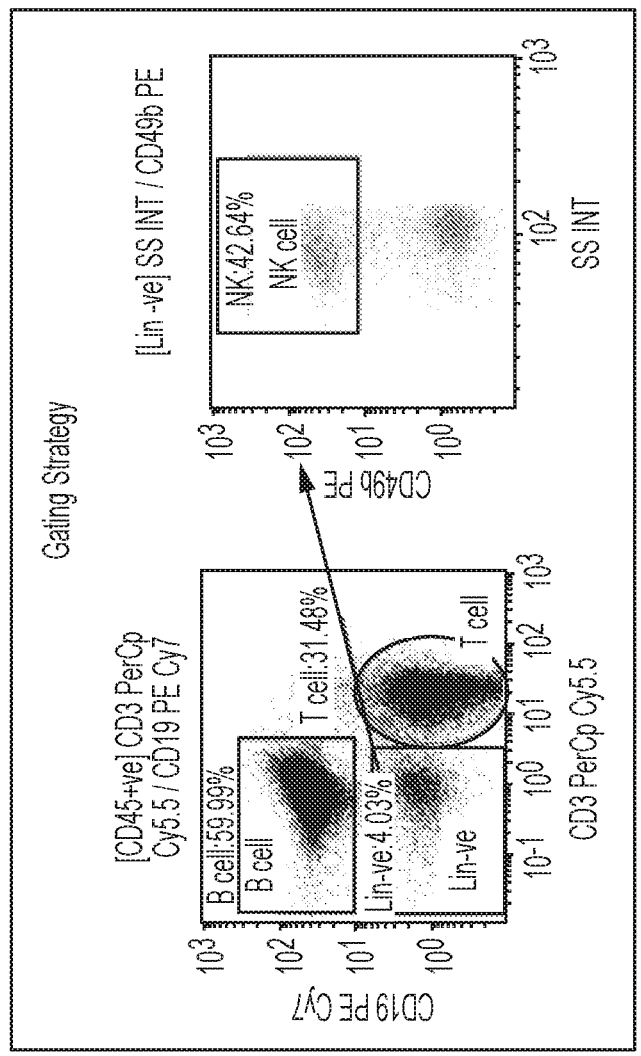
FIGS. 8A-8B: Effect of NK depletion antibody (NK1.1) on other immune cells. Intraperitoneal injection of NK1.1 was performed for 5 times according to the protocol described in method. The efficiency of NK depletion was evaluated 3 days after final injection. Splenocytes were analyzed for T cell, B cell and NK cells by flow cytometry. (A) The gating strategy used for analysis. (B) N=3 mice samples were pooled together for staining CD45, CD3, CD19, CD49b antibodies and percentage of each populations are shown in Bar diagram. Representative scatter plot shows the efficiency of NK depletion.
Figure 8B:
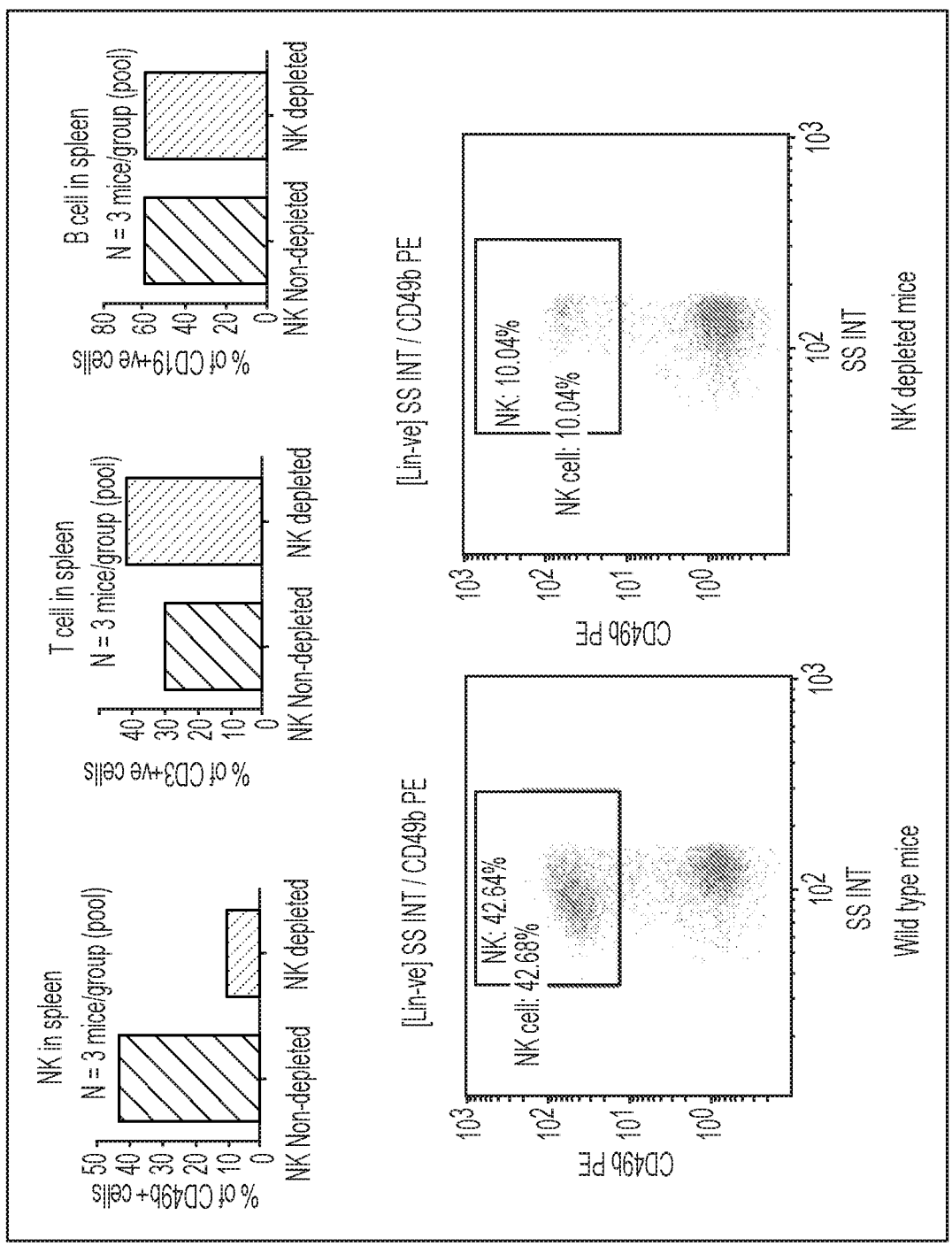
Figure 9:
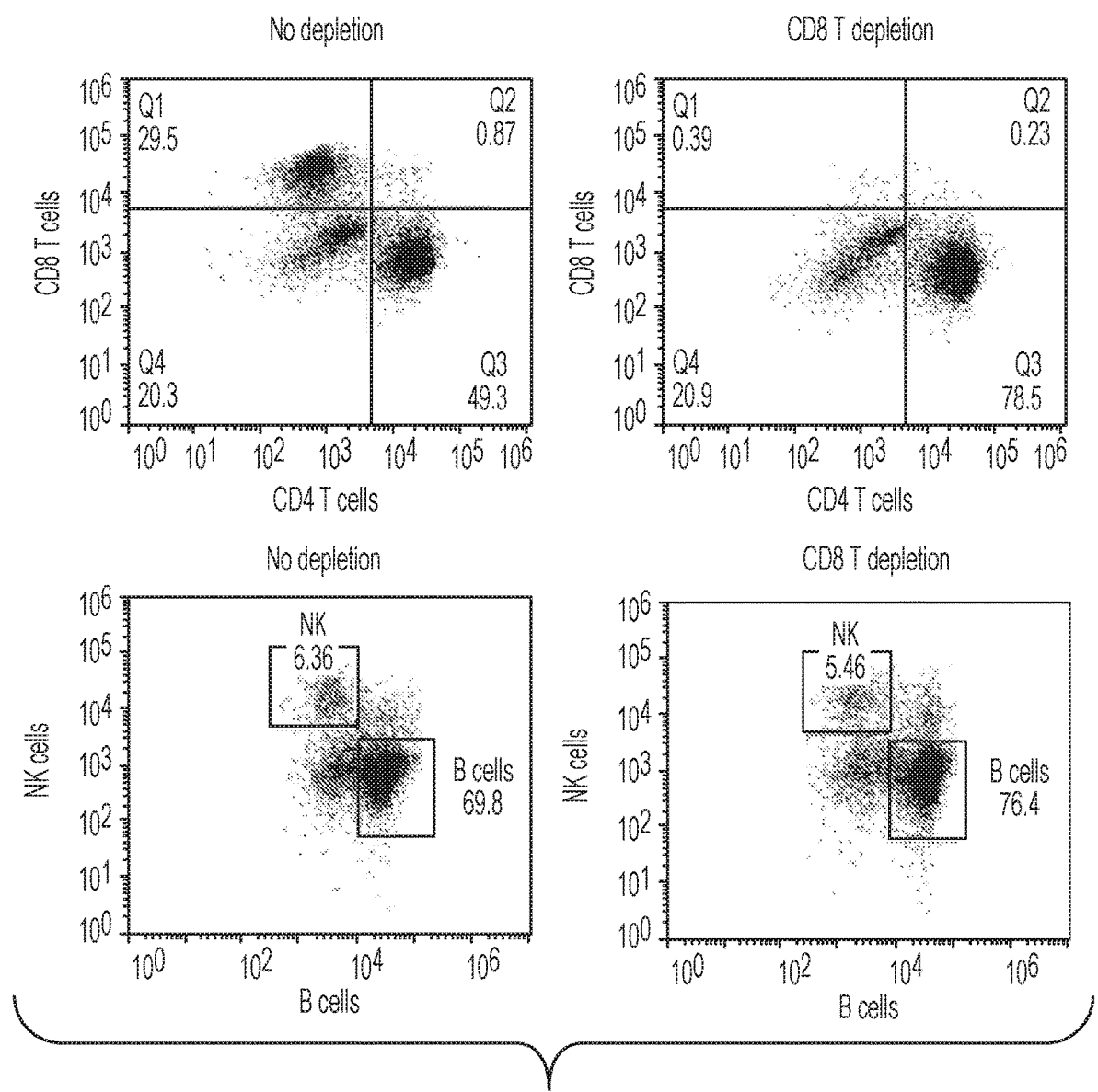
FIG. 9: Effect of CD8 T depletion on other immune cells. Intraperitoneal injection of CD8 T cells depletion antibody was performed for 5 times according to the protocol described in method. The efficiency of NK depletion was evaluated 3 days after final injection. Splenocytes were analyzed for T cell, B cell and NK cells by flow cytometry. Representative scatter plot shows the efficiency of CD8 T cells depletion without affecting other cells.

Depletion of NK or CD8+T Cells Abolishes the Anti-Tumor Effect of the Combination Completely and Partially, Respectively:

The finding that the densities of both NK and $CD^+8$ were up-regulated after combination therapy strongly suggested that $CD8^+T$ cells and NK cells regulate TUSC2+anti-PD1-induced tumor regression. To confirm this hypothesis, NK or $CD8^+T$ cells were depleted in CMT167 tumor-bearing mice via intraperitoneal injection of anti-NK1.1 or anti-$CD8^+T$ cell antibodies (FIG. 8, 9). As shown in FIG. 4A, treatment with anti-NK1.1 antibody completely abolished the tumor regression by the combination, whereas treatment with anti-$CD8^+T$ antibody partially impaired it (FIG. 4B). Also, NK cell depletion abrogated TUSC2-induced tumor growth inhibition, whereas $CD8^+T$ cells depletion had no effect. Neither depletions had any effect on anti-PD1 response. These findings suggest that while CD8+T cells might contribute TUSC2-enhanced sensitivity to anti-PD1, NK cells are indispensable for this synergy.

Next, analysis of serum cytokines using Luminex assay revealed that both TUSC2 and the combination induced a strong Th1-mediated immune response (control vs TUSC2: p<0.0001; control vs combination: p=0.007 (FIG. 4C), an effect that was abrogated with NK depletion (TUSC2 vs TUSC2/NK1.1: p=0.008; combination vs combination/NK1.1: p=0.0009) This suggests that NK cells are important in inducing Th1-mediated immune responses to TUSC2 and combination. However, with or without NK depletion, there was no significant difference in Th1/Th2 ratio in these two treatment groups. TUSC2+anti-PD1 therapy promoted higher levels of IL-15 (p=0.0001) and IL-18 (p<0.0001) cytokines compared to their untreated or anti-PD1-treated counterparts (FIG. 4D). IL-15 was induced to the same levels in TUSC2 and combination groups, whereas, IL-18 levels were significantly higher in TUSC2 than those of the combination. When NK cells were depleted, the levels of IL-15 (control vs TUSC2: p=0.03) and IL-18 (control vs TUSC2: p=0.0005) decreased significantly. With or without NK depletion, there was significant difference in the levels of IL-18 between TUSC2 and combination, but not for IL-15. Finally, expression profile of sorted NK cells and tumor tissue using qPCR and Nanostring technology showed significantly higher expression of IL-15R and IL-18R in TUSC2-treated than those of their untreated and anti-PD1-treated counterparts (p=0.01 and p=0.001 respectively; FIG. 4E, F).

Combination Treatment with TUSC2 and Anti-PD1 Enhanced Survival of Syngeneic G12D Kras-Mutant Lung Metastasis Model:

The efficacy of TUSC2+anti-PD1 was evaluated in a second Kras metastatic model using 129Sv mice intravenously inoculated with 344SQ-luciferase lung cancer cells harboring K-rasG12D mutation. The level of PD-L1 expression in 344SQ cells is only 4.5%, (FIG. 5A). The sequential treatment strategy is shown in FIG. 5B. Treatment groups were similar as with the previous model with addition of two groups, anti-PD1 combination with anti-CTLA4 and TUSC2 combination with anti-PD1 and anti-CTLA4. The former combination was used in this experiment because of reports of enhanced clinical efficacy compared with each drug alone (Larkin et al., 2015). TUSC2 significantly improved survival compared to untreated, anti-PD1, and anti-PD1+anti-CTLA4-treated groups (TUSC2 vs control: p<0.0001; TUSC2 vs anti-PD1: p<0.001; TUSC2 vs anti-PD1+anti-CTLA4: p<0.001) (FIG. 5C). When TUSC2 was combined with anti-PD1, survival was extended significantly (combination vs control: p<0.0001; combination vs anti-PD1: p<0.001; combination vs TUSC2: p=0.024). Combining TUSC2 with anti-PD1 and anti-CTLA4 extended survival few days over TUSC2+anti-PD1 treatment. Bioluminescent imaging of tumors supported these findings (FIG. 5D). FIG. 5E shows an impressive clearance of tumor nodules in the lungs given TUSC2+anti-PD1 at week 2. These results confirm efficacy of TUSC2+anti-PD1 combination, and suggest that TUSC2 combination with the dual checkpoint blockade, anti-PD1 and anti-CTLA4, has translational value.

Analysis of immune-cell infiltration using single-cell analysis showed higher NK cell infiltration by TUSC2 compared to control or anti-PD1 combination with anti-CTLA4-treated groups (p<0.001) (FIG. 5F). The effects of TUSC2+anti-PD1 or TUSC2+anti-PD1+anti-CTLA4 were slightly higher than that of TUSC2. In contrast, Treg and MDSC cell infiltrates were significantly suppressed by anti-PD1 (p=0.004; p=0.0003), an effect that was further enhanced by TUSC2 and combinations (FIGS. 5G and 5H). These results were consistent with those observed in the evaluation of the CMT 167 subcutaneous tumor model (FIG. 2).

Figure 6A:
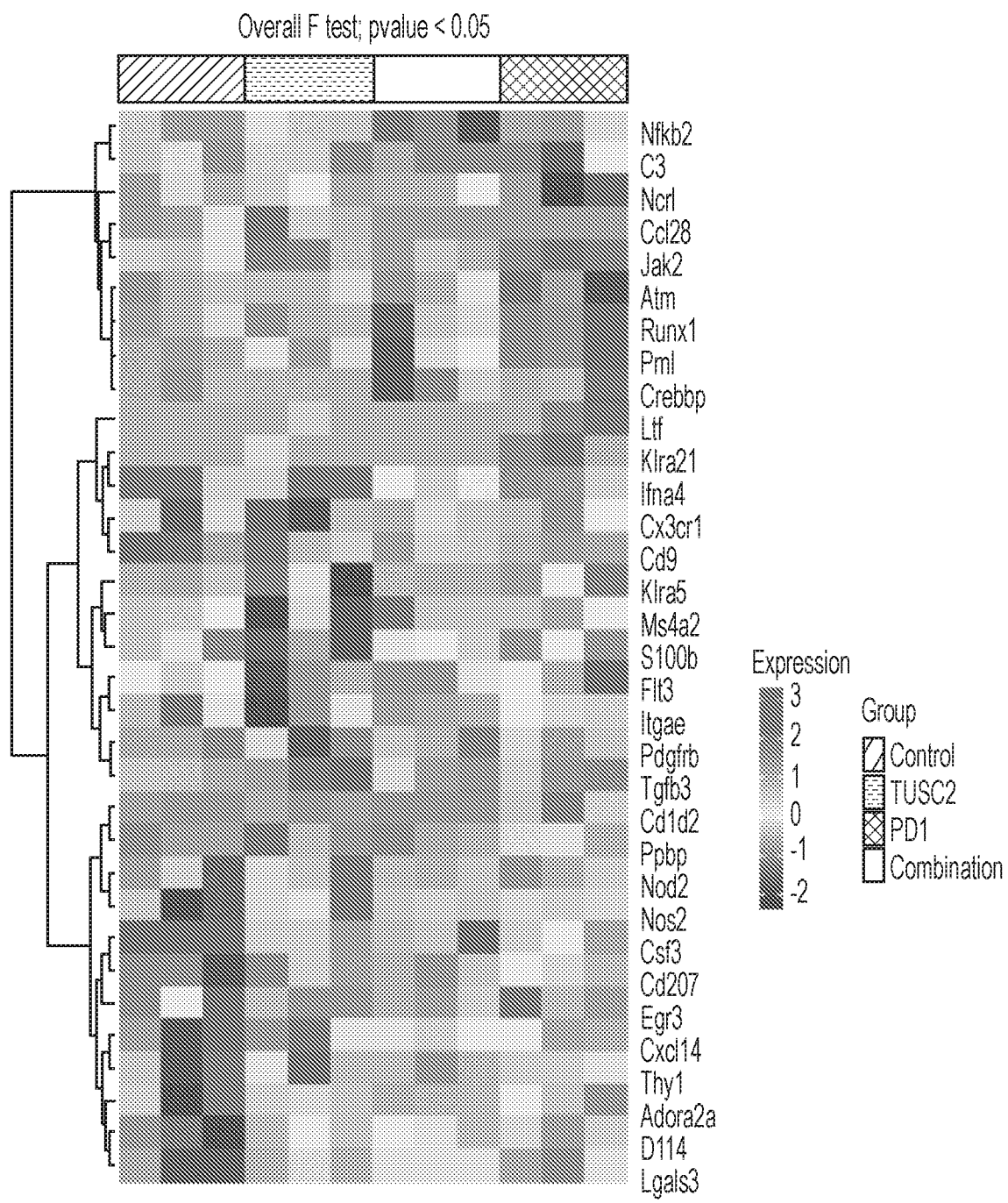
Figure 6B:
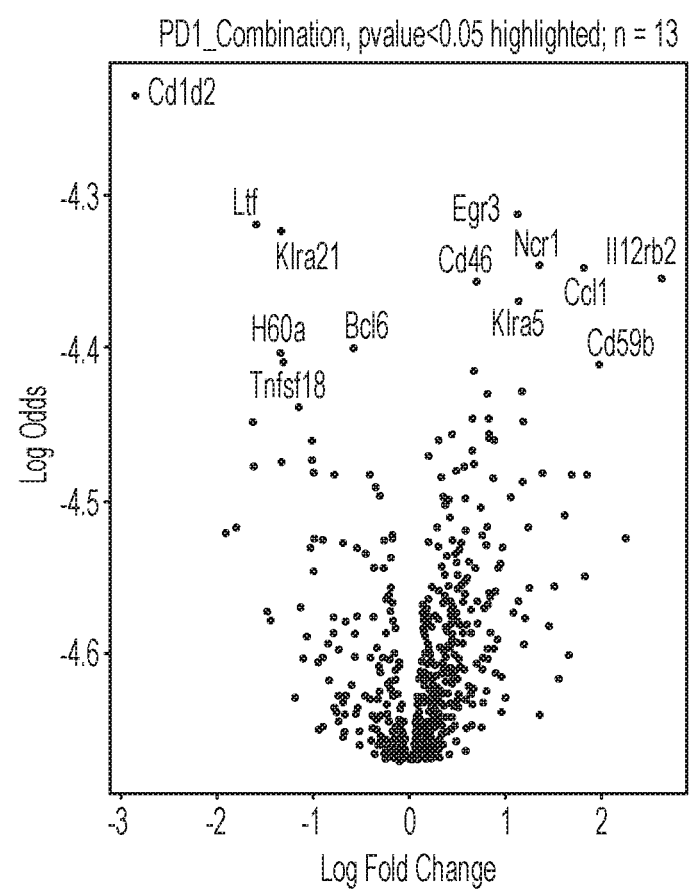
Figure 7:
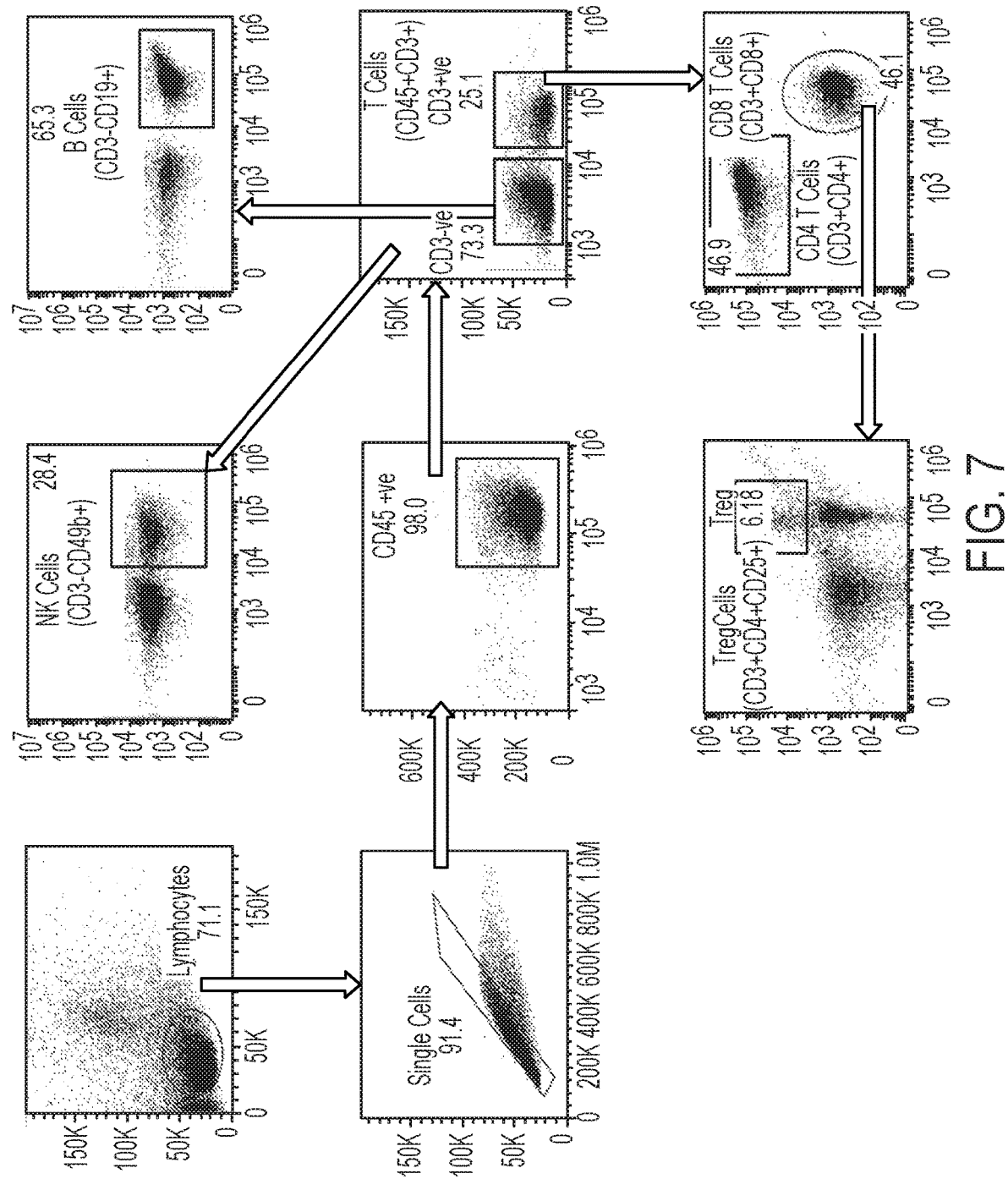
FIG. 7: Gating strategy of peripheral blood leukocytes and splenocytes was shown to determine immune subpopulations for multi-color flow cytometry assay.

TUSC2 Combination with Anti-PD1 Altered the Immune Gene Expression Profile in the Tumor Microenvironment:

To identify specific immune gene differentially expressed in TUSC2+anti-PD1 combination, RNA from tumor samples was subjected to digital multiplexed profiling using mouse pan-cancer panel consisting of 770 mouse immune genes covering both the adaptive and innate response with 40 housekeeping controls (NanoString Technologies Inc.). Welch's t-test with false discovery rate (q<0.05) correction was applied to derive statistically significant gene expression differences between treatment groups. A p-value of <0.05 was considered significant. Volcano plots and Heatmap were used to visualize the results (FIGS. 6A, B). Because TUSC2 addition enhanced response to anti-PD1 treatment, pairwise comparison was performed between anti-PD1 and TUSC2+anti-PD1 groups. Pairwise comparisons were also performed between all other groups. First, a six gene cluster was found to be significantly upregulated in the combination group. This includes Cd1d2, Ltf Klra21, H60a, Tnfsf18, and Bcl6. Another cluster was found to be significantly downregulated and consists of Egr3, Cd46, Ncr1, Klra5, Ccl1, Il2rb2, and Cd59b (FIG. 6B). All these genes are important for NK and $CD8^+T$ cell regulation (Deng et al., 2013; Shevach and Stephens, 2006; Orr et al., 2009). The combination treatment also upregulated expression of genes associated with T cell-mediated antitumor functions in the tumor microenvironment (FIG. 6D-F). These results support NK and $CD8^+T$ immunoprofiling and tumor infiltration data (FIGS. 2-3).

Example 2—Materials and Methods

Cell Culture and Reagents:

KRasG12/CMT167-luc and K-RasG12D/344SQ-luc cells were kindly provided by Drs. Alan Fields (Mayo Clinic), Frank R. Jirik (University of Calgary). Cells were cultured in Dulbecco's modified Eagle's medium supplemented with 10% fetal bovine serum (Atlanta Biological, GA) and 1% penicillin and streptomycin (life science technologies). Isotype, Anti-PD1, anti-CTLA4, InVivoPlus anti-NK1.1 (clone PK136) and anti-CD8+T (clone 2.43) anti-mouse monoclonal antibodies were purchased from Bio X Cell (West Lebanon, N.H.). DOTAP and cholesterol were purchased from Avanti Polar Lipids (Alabaster, Ala.). Synthesis and preparation of DC-TUSC2 were described previously (Ito et al., 2004).

Animal Studies:

All animal procedures were reviewed and approved by the Animal Care and Use Committee of The University of Texas MD Anderson Cancer Center. For the CMT167-luc syngeneic model, 6 to 8-week-old female C57BL/6-Elite mice (Charles River Laboratories, Houston, Tex.) were injected subcutaneously with $1\times10^6$ CMT167-luc cells in the right flank, and randomized into treatment groups, ten mice each, as follows: control (empty-vector nanovesicles, isotype antibody), anti-PD1, TUSC2 nanovesicles, and TUSC2+anti-PD1. Briefly, 25 g of TUSC2 was injected intravenously every 48 hours for 3 cycles, and 0.25 mg of anti-PD1 antibody was injected intraperitoneally (i.p.) every 4 days for 3 cycles. Tumor volumes were calculated according to the formula ½(Length×Width$^2$). Mice were euthanized at 3 to 4 weeks after tumor-cell injection, and tumors and spleen were harvested. For the 344SQ metastasis model, 6 to 8-week-old female 129/Sv mice were intravenously injected with 100,000 344SQ-luc cells. Treatment groups/ten each were: control (empty-vector nanovesicles, isotype antibody), anti-PD1, TUSC2, anti-CTLA4, TUSC2+anti-PD1, anti-PD1+anti-CTLA4, and TUSC2+anti-PD1+anti-CTLA4. For both models, animals were monitored routinely and tumors were imaged using IVIS. All treatments and measurements were double blinded. For immune phenotyping analysis, animals were killed 2 weeks after tumor-cell injection, lungs were harvested and peripheral blood was collected via cardiac puncture.

Depletion of NK or CD8+T Cells:

To deplete NK cells or CD8+T cells in tumor-bearing CMT167 mice, the neutralizing monoclonal antibodies anti-NK1.1 (clone PK136) or anti-CD8+T (clone 2.43) anti-mouse monoclonal antibodies were injected into the mice (100 μg, i.p.) every 3 days for 4 cycles beginning on day 0 after subcutaneous inoculation of tumor cells. NK or CD8+T cell depletion status was monitored via flow cytometry analysis of splenocytes. Tumor volumes were measured and tumor bioluminescence intensities were quantitated with IVIS.

Multicolor Flow Cytometry:

PBLs were isolated and cells stained according to standard protocols for flow cytometry. Multi-color panels were developed and optimized with a Gallios Flow Cytometer Research System (Beckman Coulter, Brea, Calif.). Mouse antibodies were purchased from BioLegend (San Diego, Calif.). Single-cell suspensions were washed with fluorescence-activated cell sorting staining buffer, incubated with a mouse Fc receptor-binding inhibitor for 10 min, and stained with the indicated antibodies. The data were and analyzed using FlowJo software version 10 (FlowJo, Ashland, Oreg.).

Immunohistochemistry:

CMT167-harvested tumors were fixed in 10% paraformaldehyde, and 8 m sections of formalin-fixed paraffin-embedded tissue were stained with anti-CD8, anti-Foxp3, anti-Gr-1 and anti-NKp46 mouse antibodies. All immunohistochemical analyses were performed at the MD Anderson Histology Core Laboratory (Smithville, Tex.). At least five tumor samples from each group were stained for each antibody, imaged and analyzed using a 200-slide Vectra 3.0 Automated Quantitative Pathology Imaging System (PerkinElmer, Waltham, Mass.) at the Imaging Core Facility at MD Anderson (Houston, Tex.). H-scores ranging from 0 to +3 were generated via per-cell.

Quantitative PCR:

Total RNA was extracted using an RNeasy Mini Kit (Qiagen, Hilden, Germany) and reverse transcribed using a SuperScript III kit (Invitrogen, Carlsbad, Calif.). Quantitative PCR was performed with SYBR Green PCR Master Mix (Applied Biosystems, Foster City, Calif.). Relative expression levels were normalized and expression levels were measured with an ABI Viia7 Real-Time PCR System (Applied Biosystems). The relative quantification was performed using the comparative CT method described by the manufacturer.

Luminex Assay:

To identify serum cytokines and chemokines, Affymetrix (eBioscience) ProcartaPlex 36-plex immunoassays (Affymetrix, Santa Clara, Calif.) were used according to the manufacturer's instructions. Three samples per treatment group were analyzed in duplicates. Briefly, seven standards were prepared according to the manufacturer's protocol, and 25μL of serum samples were mixed with the indicated antibody-coated beads and incubated for 2 hours at room temperature with shaking at 500 rpm. ProcartaPlex Multiplex Immunoassays used Luminex xMAP (multi-analyte profiling) technology. Plates were read using a Luminex 200 system (Luminex, Austin, Tex.) to plot the standard curve. ProcartaPlex Analyst software version 1.0 was used to analyze the data.

Gene Expression Analysis:

Extracted total tumor RNA from treatment groups, three replicates each, using a Qiagen RNeasy Mini Kit were submitted to the Genomic Core Facility at Baylor College of Medicine (Houston, Tex.) for quality control and expression profile analysis with the NanoString Technology. The NanoString PanCancer mouse immune profiling panel used profiles 776 genes related to specific immune-cell types and immune-cell functions. The data were analyzed at the Bioinformatics Core Facility at MD Anderson.

Statistical Analyses:

For the CMT167 model, generalized linear regression models were used to analyze tumor growth. All data are presented as mean±SD, and statistical significance of differences between treatments was tested by two-way ANOVA and tailed t test; $P<0.05$ was considered significant. For the 344SQ model, the distribution of overall survival (OS) was estimated by the Kaplan-Meier method. Log-rank test was performed to test the difference in survival between groups. Regression analyses of survival data based on the Cox proportional hazards model was conducted on OS defined as from the time of treatment onset to the time of death.

Statistical analyses of flow cytometry and luminex data were done by general linear regression models to compare the different treatment groups. For Immunohistochemistry data generalized linear regression models were used for statistical analysis of H scores among treatment groups. ESTIMATE statement in PROC MIXED procedure in SAS was used between each pair. For NanoString analysis, data was normalized prior to being used to quantify gene profile and statistical analysis. The positive controls, housekeeping genes and negative controls were used to adjust for sample preparation variation, background noise and RNA content variation. Linear model was used to evaluate the overall treatment effect and contrast was used to make pairwise comparisons of interest. The resulting p values were modeled using the beta-uniform mixture (BUM) model to determine a false discovery rate (FDR) cutoff and identify significantly differentially expressed genes. All statistical analyses were performed using R statistical software.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,533,254
U.S. Pat. No. 4,554,101
U.S. Pat. No. 4,728,575
U.S. Pat. No. 4,728,578
U.S. Pat. No. 4,737,323
U.S. Pat. No. 4,921,706
U.S. Pat. No. 5,030,453
U.S. Pat. No. 5,397,987
U.S. Pat. No. 5,855,911
U.S. Pat. No. 5,962,016
U.S. Pat. No. 6,413,544
U.S. Pat. No. 6,610,657
U.S. Pat. No. 6,680,068
U.S. Pat. No. 6,770,291
U.S. Pat. No. 6,770,291
U.S. Pat. No. 7,902,441
U.S. Publn. 2004/0208921
U.S. Publn. 2006/0251726
U.S. Publn. 2007/0092968
U.S. Publn. 2009/0023207
U.S. Publn. 2011/0052570
Aksentijevich et al., *Human Gene Therapy*, 7:1111-22, 1996.
Arap et al., *Cancer Res.*, 55(6):1351-1354, 1995.
Ausubel et al., *Current Protocols in Molecular Biology*, John Wiley & Sons, Inc., New York, N.Y., 1996; 1998
Bakhshi et al., *Cell*, 41(3):899-906, 1985.
Ballou et al., *Bioconjugate Chemistry*, 15:79-86, 2004.
Ben-Neriah et al., *Science*, 233:212-214, 1986.
Bishop, *Cell*, 64:235-48, 1991.
Blankenberg, *Cancer Biology & Therapy*, 7(10):1525-1532, 2008.
Brady and Dodson, *Nature*, 368:692-693, 1994.
Buchhagen et al., *Head and Neck*, 18:529-537, 1996.
Butturini et al., *Leukemia Res.*, 20(6):523-529, 1996.
Caldas et al., *Nat. Genet.*, 8(1):27-32, 1994.
Chapman et al., *Nucleic acid Res*, 19: 3979-3986, 1991.
Cheng et al., *Cancer Res.*, 54(21):5547-5551, 1994.
Cheng et al., *Invest. Radiol.*, 22(1):47-55, 1987.
Clayman et al., *Journal of Clinical Oncology*, 16:2221-32, 1998.
Cleary and Sklar, *Proc. Natl. Acad. Sci. USA*, 82(21):7439-43, 1985.
Cleary et al., *J. Exp. Med.*, 164(1):315-320, 1986.
Colledge and Scott, *Trends in Cell Biology*, 9:216-221, 1999.
Daly et al., *Oncogene*, 8:1721-1729, 1993.
Deng et al., *Cancer Res.*, 67:709-17, 2007.
Deng et al., *Oncogene*, 32:4273-83, 2013.
Drin et al., *AAPS Pharm. Sci.*, 4(4):1-7, 2002.
Du et al., *J. Pept. Res.*, 51:235-243, 1998.
Dubertret et al., *Science*, 298:1759-1762, 2002.
Dwarakanath et al., *Biochem. Biophysical Res. Commun.*, 325:739-743, 2004.
Eggermont et al., *EMBO J.*, 12: 2539-2548, 1993.
Ellerby et al. *Nature Med.*, 9:1032-1038, 1999.
Farhood et al., *Biochim. Biophys. Act*, 289-295, 1995.
Ferrari, *Nature Reviews*, 5:161-171, 2005.
Fidler and Ellis, *Cell*, 79(2):185-188, 1994.
Folkman and Shing, *J. Biol. Chem.*, 267(16):10931-10934, 1992.
Folkman, Nature Med., 1:27-31, 1995.
Frangioni, *Current Opin. Chem. Biol.*, 7:626-634, 2003.
Gazdar et al. In: *Sym. Quant. Biol.*, Cold Spring Harbor, 59:565-572, 1994.
Gazdar et al., *Intl. J. Cancer*, 78:766-774, 1998.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Goodwin et al., *J. Biol Chem.*, 267: 16330-16334, 1992.
Gorunova et al., *Genes Chrom. Cancer*, 23:81-99, 1998.
Great Britain Appln. 2193095 A
Griffith et al., *Annual review of immunology*, 32:659-702, 2014.
Gupta et al., *Biomaterials*, 26:3995-4021, 2005.
Gupta et al., *Biomaterials*, 26:3995-4021, 2005.
Gupta et al., *Biomaterials*, 26:3995-4021, 2005.
Gupta, *IEEE Trans. Nanobioscience.*, 3:66-73, 2004.
Hanahan and Folkman, *Cell*, 86(3):353-364, 1996.
Hantschel et al., *Cell*, 112:845-857, 2003.
Hollstein et al., *Science*, 253(5015):49-53, 1991.
Hope et al., 1985
Horowitz, In: *MRI Physics for Radiologists: A Visual Approach*, 1995
Hughson et al., *Cancer Genet. Cytogenet.*, 106:93-104, 1998.
Hussussian et al., *Nat. Genet.*, 8(1):15-21, 1994.
Hvalby et al., *Proc. Natl. Acad. Sci. USA*, 91:4761-4765, 1994.
Ito et al., *Mol Ther.*, 7:409-18, 2003.
Ito et al., *Cancer Gene Ther.*, 11:733-9, 2004.
Ivanova et al, *J Pathol*, 211: 591-601, 2007.
Jameson et al., *Nature* 368: 744-746, 1994
Ji et al., *Cancer Res.*, 62:2715-2720, 2000.
Ji et al., *Cancer Res.*, 62:2715-20, 2002.
Ji et al., *Future Oncology*, 1:79-92, 2005.
Ji et al., *Journal of Thoracic Oncology.*, 327-30 10.1097/JTO.0b013e31816bce65, 2008.
Johnson et al., *J. Virol.*, 67:438-445, 1993.
Kamb et al., *Nat. Genet.*, 8(1):23-26, 1994.
Kamb et al., *Science*, 2674:436-440, 1994.
Kerr et al., *Br. J. Cancer*, 26(4):239-257, 1972.
Kerr et al., *Br. J. Cancer*, 26(4):239-257, 1972.
Kersemaekers et al., *Intl. J. Cancer*, 79:411-417, 1998.
Kloetzer et al., *Virology*, 140(2):230-238, 1985.

Kohno et al., *Cancer*, 85:341-347, 1999.
Kondo et al., *Oncogene*, 20:6258-6262, 2001.
Kondo et al., *Oncogene*, 20:6258-6262, 2001.
Kyte and Doolittle, *J. Mol. Biol.*, 157(1):105-132, 1982.
Lerman et al., *Cancer Res.*, 60:6116-33, 2000.
Lewin et al., *Nat. Biotechnol.*, 18:410-414, 2000.
Lin et al., *Oncogene*, 20:1873-1881, 2001.
Ling et al., *Cancer Res.*, 63:298-303, 2003.
Liposome Technology, Gregoriadis (Ed.), Boca Raton, Fla., CRC Press, 1984.
Lowe et al., *Nature*, 2004; 432:307-15, 2004.
Mabry et al., In: *Lung Cancer in the Genetic Basis of Human Cancer*, Vogelstein and Kinzler (Eds.), McGraw Hill, 671-679, 1998.
Mayer et al., *Biochim. Biophys. Acta*, 858(1):161-168, 1986.
Mayhew et al., *Biochim. Biophys. Acta*, 775(2):169-174, 1984.
Mayhew et al., *Methods Enzymol.*, 149:64-77, 1987.
Michalet et al., *Science*, 307:538-544, 2005.
Miller et al., *Cancer*, 47:207-214, 1981.
Miller et al., *Oncogene*, 22:6006-6013, 2003.
Minna et al., In: *Cancer: Principles and Practice of Oncology*, 5$^{th}$ Ed., Philadelphia: Lippincott, 849-857, 1997.
Morawski et al., *Current Opinion Biotech.*, 16, 89-92, 2005.
Mori et al., *Cancer Res.*, 54(13):3396-3397, 1994.
Nishihara et al., *Cancer Letter*, 180(1):55-61, 2002.
Nobri et al., *Nature (London)*, 368:753-756, 1995.
Obenauer et al., *Nucleic Acids Res.*, 31(13):3635-3641, 2003.
Okamoto et al., *Proc. Natl. Acad. Sci. USA*, 91(23):11045-11049, 1994.
Orlow et al., *Cancer Res*, 54(11):2848-2851, 1994.
Orlow et al., *Int. J. Oncol.*, 15(1):17-24, 1994.
Orr et al., *The Journal of experimental medicine*, 206:807-17, 2009.
O'Quigley J et al., *Biometrics*, 46:33-48, 1990.
PCT Appln. PCT/US85/01161
PCT Appln. PCT/US89/05040
PCT Appln. WO 02/100435A1
PCT Appln. WO 03/015757A1
PCT Appln. WO 04/002453A1
PCT Appln. WO 04029213A2
Pure & Appl. Chem., 63(3):427-463, 1991.
Ramesh et al., *Mol Ther.*, 3:337-50, 2001.
Remington's Pharmaceutical Sciences" 15th Edition, pages 1035-1038 and 1570-1580, 1990.
Roberts et al., *Adv. Drug Del. Rev.*, 54(4):459-476, 2002.
Rojas et al., *J. Biol. Chem.*, 271:27456-27461, 1996.
Rojas et al., *Nature Biotechnol.*, 16:370-375, 1998.
Roth et al., *Nat Med.*, 2:985-91, 1996.
Roth, *Forum*, 8:368-376, 1998.
Roth, *Expert Opinion on Biological Therapy*, 6:55-61, 2006.
Sambrook et al., In: *Molecular Cloning: A Laboratory Manual*, 2nd Ed., Cold Spring Harbor Press, Cold Spring Harbor, N.Y., 1989
Schwarze et al., *Science*, 285:1569-1572, 1999.
Schwarze et al., *Trends Cell Biol.*, 10:290-295, 2000.
Sekido et al., *Biochimica. Biophysica. Acta*, 1378:F21-F59, 1998.
Sekido et al., *Oncogene*, 16:3151-3157, 1998.
Sekido et al., *Proc. Natl. Acad. Sci. USA*, 93:4120-4125, 1996.
Serrano et al., *Nature*, 366:704-707, 1993.
Serrano et al., *Science*, 267(5195):249-252, 1995.
Sestier et al., *Electrophoresis*, 19:1220-1226, 1998.
Shevach and Stephens, *Nature reviews Immunology*, 6:613-8, 2006.
Simberg et al., *Human Gene Therapy*, 16:1087-96, 2005.
Simberg et al., *Proceedings of the National Academy of Sciences*, 104:932-6, 2007.
Spandidos et al., *Anticancer Res.*, 9(2):383-386, 1989.
Stayton et al., *J. Controlled Release*, 65:203-220, 2000.
Sun et al., *Biopolymers*, 60(1):61-75, 2001.
Swisher et al., *J Natl Cancer Inst.*, 91:763-71, 1999.
Templeton, *Nature Biotech.*, 15:647-652, 1997.
Templeton, *Nature Biotechnology*, 15:647-652, 1997.
Travali et al., *FASEB J.*, 4(14):3209-3214, 1990.
Tsujimoto and Croce, *Proc. Natl. Acad. Sci. USA*, 83(14):5214-5218, 1986.
Tsujimoto et al., *Science*, 228(4706):1440-1443, 1985.
Uno et al., *Cancer Research*, 64:2969-2976, 2004.
Uzawa et al., *Cancer Genet. Cytogenet.*, 107:125-131, 1998.
Viola et al., *Trends in immunology*. 33:496-504, 2012.
Virmani et al., *Genes Chrom Cancer*, 21:308-319, 1998.
Wang, *Oncogene*, 19(49):5643-5650, 2000.
Weinberg, *Science*, 254(5035):1138-1146, 1991.
Weinberg, *Science*, 254:1138-1146, 1991.
Wen and Van Etten, *Genes and Development*, 11:2456-2467, 1997.
West, *Methods in Molec. Biol.*, 238:113-122, 2004.
Wilhelm et al., *Biomaterials*, 24:1001-1011, 2003.
Wistuba et al., *Cancer Res.*, 57:3154-3158, 1997.
Wistuba et al., *Cancer Res.*, 59:1973-1979, 1999.
Wistuba et al., *Oncogene*, 18:643-650, 1999.
Woodring et al., *J. Cellular Science*, 116(Pt. 13):2613-2626, 2003.
Zbar et al., *Nature*, 327:721-724, 1987.
Yang et al., *Gene Ther.*, 4:950-60, 1997.
Zhao, *Anti-Cancer Agents in Medicinal Chemistry*, 9:1018-1023, 2009.

What is claimed is:

1. A method treating a subject having a cancer comprising administering a TUSC2 therapy to the subject, wherein the TUSC2 therapy comprises administration of a TUSC2 expression vector, and wherein the subject has been or is being treated with at least one anti-PD1 antibody.

2. The method of claim 1, further comprising administering at least one immune checkpoint inhibitor to the subject.

3. The method of claim 2, wherein the administering at least one immune checkpoint inhibitor to the subject comprises administering the at least one immune checkpoint inhibitor before the TUSC2 therapy.

4. The method of claim 2, wherein the administering at least one immune checkpoint inhibitor to the subject comprises administering the at least one immune checkpoint inhibitor after or concomitantly with the TUSC2 therapy.

5. The method of claim 2, wherein the subject was administered the at least one immune checkpoint inhibitor no more than two weeks before the TUSC2 therapy.

6. The method of claim 2, wherein the subject has been or is being treated with two immune checkpoint inhibitors.

7. The method of claim 1, wherein the TUSC2 therapy is administered two or more times.

8. The method of claim 1, further comprising administering an anti-inflammatory agent.

9. The method of claim 1, further comprising administering a further anti-cancer therapy to the subject.

10. The method of claim 1, wherein the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer.

11. The method of claim 1, wherein the cancer is resistant to a least a first chemotherapy.

12. The method of claim 2, wherein administering the TUSC2 therapy and at least one immune checkpoint inhibitor results in an increase of NK and/or $CD8^+T$ cell density in the tumor.

13. The method of claim 2, wherein administering the TUSC2 therapy and at least one immune checkpoint inhibitor results in an increase in CcL3, CcL4, CcL21a, and/or CcL19 serum levels.

* * * * *

UNITED STATES PATENT AND TRADEMARK OFFICE
CERTIFICATE OF CORRECTION

PATENT NO. : 11,278,592 B2
APPLICATION NO. : 16/341134
DATED : March 22, 2022
INVENTOR(S) : Roth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 176 days.

Signed and Sealed this
Twenty-ninth Day of November, 2022

Katherine Kelly Vidal
Director of the United States Patent and Trademark Office